United States Patent
Westoby et al.

(10) Patent No.: US 11,697,670 B2
(45) Date of Patent: Jul. 11, 2023

(54) METHODS FOR PURIFYING ANTIBODIES HAVING REDUCED HIGH MOLECULAR WEIGHT AGGREGATES

(71) Applicant: Biogen MA Inc., Cambridge, MA (US)

(72) Inventors: Matthew Westoby, Chapel Hill, NC (US); Greg Evangelist, Cary, NC (US)

(73) Assignee: Biogen MA Inc., Cambridge, MA (US)

( * ) Notice: Subject to any disclaimer, the term of this patent is extended or adjusted under 35 U.S.C. 154(b) by 367 days.

(21) Appl. No.: 16/640,755

(22) PCT Filed: Aug. 22, 2018

(86) PCT No.: PCT/US2018/047609
§ 371 (c)(1),
(2) Date: Feb. 21, 2020

(87) PCT Pub. No.: WO2019/040671
PCT Pub. Date: Feb. 28, 2019

(65) Prior Publication Data
US 2021/0130397 A1 May 6, 2021

Related U.S. Application Data

(60) Provisional application No. 62/548,962, filed on Aug. 22, 2017.

(51) Int. Cl.
| | | |
|---|---|---|
| *C07K 1/14* | (2006.01) |
| *C07K 1/36* | (2006.01) |
| *C07K 16/00* | (2006.01) |
| *C07K 1/18* | (2006.01) |
| *C07K 1/20* | (2006.01) |

(Continued)

(52) U.S. Cl.
CPC .......... *C07K 1/18* (2013.01); *A61K 39/39591* (2013.01); *C07K 1/14* (2013.01); *C07K 1/20* (2013.01); *C07K 1/22* (2013.01); *C07K 1/36* (2013.01); *C07K 16/00* (2013.01); *C07K 16/065* (2013.01)

(58) Field of Classification Search
CPC .. A61K 39/39591; C07K 1/1136; C07K 1/14; C07K 1/36; C07K 16/00; C07K 16/065
See application file for complete search history.

(56) References Cited

U.S. PATENT DOCUMENTS

| 2006/0134694 A1* | 6/2006 | Yamakawa | ............ B82Y 10/00 |
|---|---|---|---|
| | | | 435/7.1 |
| 2013/0197198 A1 | 8/2013 | Sun et al. | |

(Continued)

FOREIGN PATENT DOCUMENTS

| WO | 2009/009532 A2 | 1/2009 | |
|---|---|---|---|
| WO | WO-2009009523 A2 * | 1/2009 | ....... A61K 39/39591 |

OTHER PUBLICATIONS

International Search Report and Written Opinion for Application No. PCT/US2018/047609 dated Oct. 30, 2018.

(Continued)

*Primary Examiner* — Jeffrey E. Russel
(74) *Attorney, Agent, or Firm* — Wolf, Greenfield & Sacks, P.C.

(57) ABSTRACT

Provided herein, in some embodiments, are methods and compositions for purifying antibodies from cellular cultures using one or more thiol containing additives during a purification process, for example in a chromatographic purification process.

13 Claims, 13 Drawing Sheets

(51) Int. Cl.
   *C07K 1/22*     (2006.01)
   *C07K 16/06*    (2006.01)
   *A61K 39/395*   (2006.01)

(56) References Cited

U.S. PATENT DOCUMENTS

| | | | |
|---|---|---|---|
| 2014/0179904 | A1 | 6/2014 | Arunakumari et al. |
| 2015/0274808 | A1 | 10/2015 | Evans et al. |
| 2015/0361130 | A1 | 12/2015 | Shultz et al. |
| 2016/0016992 | A1 | 1/2016 | Bian et al. |
| 2017/0058019 | A1 | 3/2017 | Felfoldi et al. |
| 2017/0137500 | A1 | 5/2017 | Allison et al. |
| 2019/0284281 | A1* | 9/2019 | Krebs .................... A61P 29/00 |

OTHER PUBLICATIONS

International Preliminary Report on Patentability for Application No. PCT/US2018/047609 dated Mar. 5, 2020.

Extended European Search Report for Application No. 18848414.1 dated Aug. 13, 2021.

Chung et al., Effects of antibody disulfide bond reduction on purification process performance and final drug substance stability. Biotechnol Bioeng. Jun. 2017;114(6):1264-1274. doi: 10.1002/bit.26265. Epub Mar. 6, 2017.

Shukla et al., Downstream processing of monoclonal antibodies—application of platform approaches. J Chromatogr B Analyt Technol Biomed Life Sci. Mar. 15, 2007;848(1):28-39. doi: 10.1016/j.jchromb.2006.09.026. Epub Oct. 13, 2006.

Vázquez-Rey et al., Aggregates in monoclonal antibody manufacturing processes. Biotechnol Bioeng. Jul. 2011;108(7):1494-508. doi: 10.1002/bit.23155. Epub Apr. 20, 2011.

PCT/US2018/047609, Oct. 30, 2018, International Search Report and Written Opinion.

PCT/US2018/047609, Mar. 5, 2020, International Preliminary Report on Patentability.

\* cited by examiner

METHODS FOR PURIFYING ANTIBODIES HAVING REDUCED HIGH MOLECULAR WEIGHT AGGREGATES

CROSS-REFERENCE TO RELATED APPLICATION

This application is a national stage filing under 35 U.S.C. § 371 of International Patent Application Serial No. PCT/US2018/047609, filed Aug. 22, 2018, which claims priority under 35 U.S.C. § 119(e) to U.S. provisional patent application, U.S. Ser. No. 62/548,962, filed Aug. 22, 2017, the contents of which are incorporated herein by reference in their entirety.

FIELD OF THE INVENTION

Methods and compositions described herein relate to antibody purification technology.

BACKGROUND

Monoclonal antibodies (Mabs) are used in treatment of a wide range of diseases, Thus, efficient methods for purifying Mabs in high concentrations and with high purity are needed. Mab purification and purity may be hindered, in part, by high molecular weight (HMW) antibody aggregates. Formation of such aggregates compromises biological activity, thereby leading to partial or complete loss of Mab therapeutic effectivity. Aggregates also may trigger an immunogenic reaction from a patient. Accordingly, processes for purifying antibodies having reduced high molecular weight aggregates are needed.

SUMMARY OF THE INVENTION

Aspects of the disclosure provide methods and compositions for purifying an antibody by subjecting an antibody sample to a purification procedure, wherein the purification procedure includes a thiol containing additive in one or more steps.

The present disclosure is based, in part, on the finding that thiol containing additives prevented and/or reduced the formation of high molecular weight (HMW) antibody aggregates during one or more steps of an antibody purification. This provides several improvements to antibody purification methods, including the ability to increase intermediate hold times during purification, improved antibody stability at higher pH during intermediate holds and during other purification operations, the ability to perform purification steps at higher pH ranges while maintaining protein stability, and improved antibody stability during long-term storage (e.g., a day, a week, a month, a year, or longer). In some embodiments, improved antibody stability (and/or reduced aggregate formation) allows for higher antibody concentrations to be loaded onto ion exchange (e.g., anion exchange) chromatographic columns and/or hydrophobic interaction chromatographic columns.

In one aspect, the disclosure provides a method for reducing the formation of HMW antibody aggregates during one or more steps of an antibody purification. In one embodiment, the method comprises collecting an antibody sample as an eluate from a first chromatography column, and incubating the antibody sample from as an eluate for a hold time prior to loading the antibody sample onto a second chromatography column, wherein the antibody sample comprises a thiol containing additive during the hold time. In certain embodiments, the formation of high molecular weight antibody aggregates in the antibody sample is reduced relative to an antibody sample without a thiol containing additive incubated for the hold time prior to loading the antibody sample without a thiol containing additive onto a second chromatography column.

In one embodiment, the method comprises subjecting an antibody sample to viral inactivation at a pH of less than 5.0, neutralizing the antibody sample to produce a neutralized antibody sample having a pH of greater than 5.0, and introducing a thiol containing additive into the neutralized antibody sample. In certain embodiments, the formation of high molecular weight aggregates in the neutralized antibody sample is reduced relative to a neutralized antibody sample without introduction of a thiol containing additive.

In one embodiment, the method comprises introducing a thiol containing additive into an antibody sample, wherein the thiol containing additive comprises oxidized and reduced forms of the thiol containing additive in a ratio of between 1:1 and 1:10 and subjecting the antibody sample to at least one chromatographic separation. In certain embodiments, the formation of high molecular weight aggregates in the antibody sample subjected to the at least one chromatographic separation is reduced relative to an antibody sample subjected to the at least one chromatographic separation without introduction of a thiol containing additive.

In some embodiments, one or more thiol containing additives are added to an antibody containing solution obtained from one or more chromatographic separation steps (e.g., to an antibody containing solution eluted from a chromatography column).

In some embodiments, a purification procedure comprises one or more chromatographic separations. In some embodiments, the one or more chromatographic separations comprise one or more affinity chromatography, ion exchange chromatography, and/or hydrophobic interaction chromatography separations. In some embodiments, the affinity chromatography comprises Protein A chromatography. In some embodiments, the ion exchange chromatography comprises anion exchange chromatography.

In some embodiments, a thiol containing additive is added to an antibody containing solution obtained from one or more chromatographic separations. In some embodiments, the one or more chromatographic separations are performed sequentially or simultaneously.

In some embodiments, a thiol containing additive is added to an antibody containing solution (e.g., eluate) obtained from a Protein A column. In some embodiments, anion exchange chromatography that is performed on an antibody containing solution obtained from a Protein A column is performed at a pH above 7 (e.g., between 7 and 9, for example between 7 and 8.5).

In some embodiments, anion exchange chromatography is performed at a pH of at least 7. In some embodiments, anion exchange chromatography is performed at a pH of at least 7.5. In some embodiments, anion exchange chromatography is performed at a pH of at least 8.

In some embodiments, a thiol containing additive is added to an antibody containing solution after anion exchange chromatography and/or after hydrophobic interaction chromatography.

In some embodiments, an antibody containing solution is subjected to viral inactivation during the purification procedure. In some embodiments, viral inactivation is performed after Protein A chromatography. In some embodiments, a thiol containing additive is added to the antibody containing solution that is subjected to viral inactivation.

In some embodiments, the purification procedure comprises a filtration and/or antibody concentration step. In some embodiments, a thiol containing additive is added to the antibody containing solution that is being filtered and/or concentrated.

In some embodiments, a purification method further comprises determining a level of high molecular weight (HMW) aggregates of antibody in an antibody containing solution during the purification procedure. In some embodiments, the level of high molecular weight (HMW) aggregates of the antibody is reduced compared to a control level. In some embodiments, the control level is a level of HMW aggregates of the antibody in an antibody solution during a purification procedure performed in the absence of a thiol containing additive.

In some embodiments, the chromatographic separation is performed at a pH of at least 3.5 (e.g., pH 3.5 or higher, for example up to pH 5.7, 7.5, 8.0, or 8.5). In some embodiments, the chromatographic separation is performed at a pH of at least 5.7 (e.g., pH 5.7 or higher, for example up to pH 7.1, 7.5, 8.0, or 8.5). In some embodiments, the chromatographic separation is performed at a pH of at least 7.1 (e.g., pH 7.1 or higher, for example up to pH 7.5, 8.0, or 8.5).

In some embodiments, the thiol containing additive is glutathione. In some embodiments, the glutathione is selected from the group consisting of oxidized glutathione, reduced glutathione, and a combination of oxidized glutathione and reduced glutathione.

In some embodiments, the combination of oxidized glutathione and reduced glutathione is at a ratio of 1:1. In some embodiments, the combination of oxidized glutathione and reduced glutathione is at a ratio of 1:5. In some embodiments, the combination of oxidized glutathione and reduced glutathione is at a ratio of 1:10.

In some embodiments, the antibody is stable for about 12 hours or more in an antibody containing solution during the purification procedure. In some embodiments, the antibody is stable for about 24 hours or more in an antibody containing solution during the purification procedure. In some embodiments, the antibody is stable for about 48 hours or more in an antibody containing solution during the purification procedure. In some embodiments, the antibody is stable for about 72 hours or more in an antibody containing solution during the purification procedure.

These and other aspects of the technology are illustrated by the following non-limiting drawings, and described in more detail in the detailed description and examples.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

DETAILED DESCRIPTION OF THE INVENTION

Figure 1:
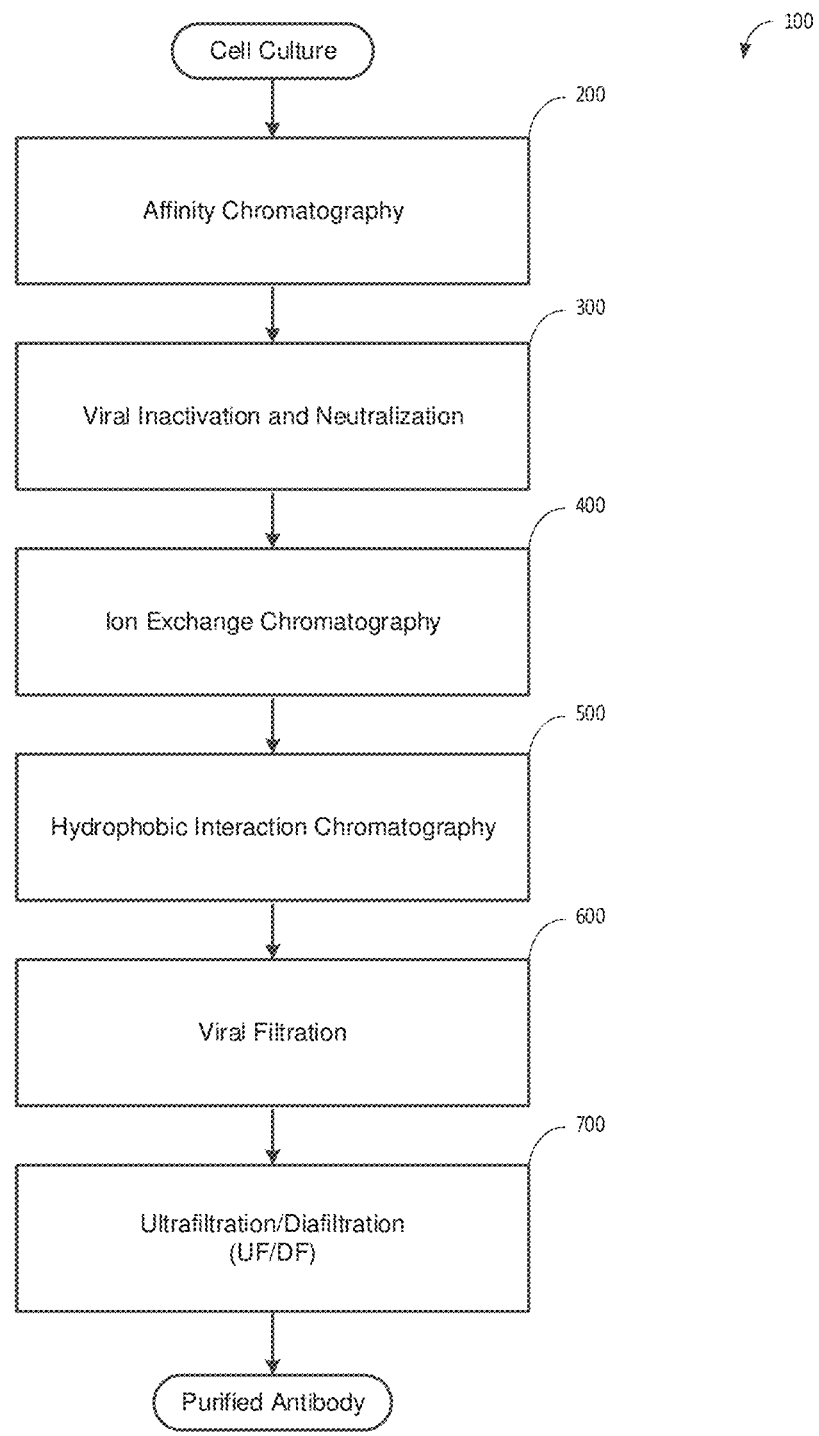
FIG. 1 is a flowchart of an exemplary method for purifying an antibody, in accordance with some embodiments of the technology described herein.

Aspects of the present application relate to methods and compositions for purifying antibodies. In some embodiments, the incorporation of thiol containing additives in one or more purification steps (e.g., by adding additive to one or more antibody solutions obtained from one or more chromatography steps) significantly improves the performance of the purification process. In some embodiments, the use of thiol containing additives during antibody purification prevents and/or reduces the formation of high molecular weight (HMW) antibody aggregates during and/or after purification.

An antibody sample, in some embodiments, refers to any mixture (e.g., sample) comprising an antibody. For example, an antibody sample is a cell culture comprising an antibody or a lysate of a cell culture comprising an antibody. In another example, an antibody sample is a mixture comprising an antibody that is subjected to at least one chromatographic separation. In some embodiments, an antibody sample is a mixture comprising an antibody that is eluted from a chromatographic resin. In some embodiments, an antibody sample is a mixture comprising an antibody that is subjected to viral inactivation. In some embodiments, an antibody sample is a mixture comprising an antibody that is subjected to filtration and/or dialysis. It should be appreciated that an antibody sample, in some embodiments, may be a solid, a liquid, a suspension, a solution, an emulsion, or a combination thereof. An antibody sample is not limited with respect to mixture type (e.g., a suspension mixture, a colloidal mixture, a solution).

Accordingly, methods and compositions provided herein provide certain advantages over conventional chromatography. In some embodiments, methods and compositions are useful to reduce percentages of high molecular weight (% HMW) antibody aggregates. In some embodiments, methods and compositions are useful to reduce % HMW antibody aggregates during chromatographic separation (e.g., during hold times). In some embodiments, methods and compositions are useful for processing antibody samples that have high concentrations of antibodies, for example by allowing high antibody concentrations to be separated via chromatography. In some embodiments, methods and compositions are useful to reduce % HMW antibody aggregates in concentrated antibody solutions. In some embodiments, methods and compositions are useful to reduce % HMW antibody aggregates during antibody storage (e.g., during intermediate steps of a purification procedure). In some embodiments, methods and compositions are useful to increase antibody yield.

In some embodiments, thiol containing additives may provide anti-oxidant effects. However, in some embodiments, thiol containing additives may prevent aggregation in addition to or without involving anti-oxidant properties. Without wishing to be bound by theory, it is believed that thiol containing additives (e.g., glutathione) can prevent carbonyl sites in an antibody from interacting to form aggregates. In some embodiments, interactions between thiol containing additives and carbonyl sites in an antibody are believed to be a major cause of decreased aggregate formation. Thus, thiol containing additives may be suitable to prevent aggregation of any protein susceptible to carbonylation. In some embodiments, it is believed that thiol containing additives block carbonyl sites on the protein, which are formed in cell culture, from reacting to form aggregated species.

In some embodiments, a thiol containing additive (e.g., glutathione) is added to one or more steps of an antibody purification procedure. An antibody can be purified from a mixture containing the antibody (e.g., from a sample of a cell culture that expresses the antibody) using one or more chromatographic steps. For example, an antibody containing sample can be added to a column containing a chromatographic resin and subsequently eluted from the column in an eluent volume (e.g., optionally after flowing a wash solution through the column). In some embodiments, a thiol containing additive is added to an antibody solution eluted from a column (e.g., from a Protein A column, from an ion exchange column, or from a hydrophobic interaction column). In some embodiments, a thiol containing additive is added to an antibody solution being processed (e.g., to inactivate viruses, to concentrate the antibody, or during other manipulations of the antibody solution) between separation steps on chromatography columns. However, a thiol containing additive can be included in one or more (e.g., a subset or all) of the solutions used during the chromatographic steps. In some embodiments, a thiol containing additive can be added to one or more of the antibody sample, to the chromatographic resin (e.g., by equilibrating the column with a solution containing the additive), to a wash solution, and/or to an antibody-containing eluent obtained from the column. In some embodiments, an antibody purification procedure includes two or more chromatographic steps, and optionally one or more additional steps, and a thiol containing additive may be included in one or more of the steps. However, in some embodiments a thiol containing additive is added to an antibody containing solution only in one or more of the intermediate steps after or between column runs. In some embodiments, the same thiol containing additive can be used in two or more steps (e.g., in all or a subset of the steps) of a purification process. In some embodiments, the same thiol containing additive is used at the same concentration in different steps, but it also may be used at different concentrations in different steps. In some embodiments, a different thiol containing additive can be used in different steps of a purification process. In some embodiments, two or more (e.g., 2, 3, 4, 5, or more) thiol containing additives can be used in each of one or more purification steps.

FIG. 1 illustrates a non-limiting embodiment of an antibody purification process 100 that involves several chromatographic separation steps and several intermediate steps between chromatography column runs. In some embodiments, purification process 100 begins with an antibody mixture (e.g., antibody sample) obtained, for example, from a cell culture (e.g., from a culture of a recombinant cell that expresses an antibody of interest). The antibody mixture (e.g., antibody sample) can be obtained from a cell culture lysate and/or a cell culture supernatant. In some embodiments, the antibody mixture (e.g., antibody sample) is a solution that contains the antibody of interest and additional components from the cell culture (e.g., host cell nucleic acids, lipids, other proteins, etc., or any combination thereof).

In some embodiments, the purification process involves an initial affinity chromatography step 200 in which a mixture comprising the antibody (e.g., a loading solution) is contacted with an affinity chromatographic resin (e.g., a Protein A chromatography resin) to remove host cell proteins (HCPs) from the mixture comprising the antibody.

Prior to contact or following contact with the antibody, the affinity chromatography resin may be washed with wash solution, for example, to remove impurities. An antibody containing solution may be eluted from the affinity chromatography resin using any method known in the art. For example, an antibody may be eluted from a Protein A chromatographic resin using a low pH solution (e.g., at a pH of about 3.5).

In some embodiments, a thiol containing additive is added to the antibody containing eluent following elution of the antibody from the resin in 200. In some embodiments, affinity chromatography 200 also is performed in the presence of a thiol containing additive. A thiol containing additive may be added at one or more steps during chromatography 200. In some embodiments, a thiol containing additive may be added to a loading solution, to a wash solution, to an elution solution, or to a combination thereof. In some embodiments, a thiol containing additive can be added to the chromatographic resin, for example, by equilibrating the column with a solution containing the additive. In some embodiments, a thiol containing additive may be added to an elution solution prior to eluting the antibody. However, in some embodiments the thiol containing additive is not included in one or more of the resin equilibration and/or washing solutions. In some embodiments, the thiol containing additive is only added to the antibody containing solution eluted from a column in 200.

In some embodiments, an elution solution comprising antibody from step 200 may be subjected to viral inactivation and neutralization (VIN) in step 300 to reduce or eliminate viral contamination. In some embodiments, a thiol containing additive may be added before, during, or after VIN step 300.

An antibody solution from step 300 then may be subjected to one or more additional chromatographic separations. One or more of the additional chromatographic separations may be performed in the presence of a thiol containing additive.

For example, an antibody may be further separated from HCPs and cellular DNA by ion exchange chromatography 400 followed by hydrophobic interaction chromatography 500. In some embodiments, a thiol containing additive is added to an antibody containing elution solution from a column in 400 and/or 500. In some embodiments, ion exchange chromatography 400 and/or hydrophobic interaction chromatography 500 also may be performed in the presence of thiol containing additive. As for chromatography 200, a thiol containing additive may be added to an antibody containing solution prior to loading on either column, added to a column wash solution, added to an eluent solution from either column, and/or equilibrated with either column prior to loading the antibody containing solution. However, in some embodiments the thiol containing additive is not included in one or more of the resin equilibration and/or washing solutions. In some embodiments, the thiol containing additive is only added to the antibody containing solution eluted from a column in 400 and/or 500.

Following one or more chromatographic separations, an antibody containing solution may be subjected to viral filtration 600 to remove viruses from the solution. Viral filtration 600 may be performed in the absence or presence of a thiol containing additive.

In some embodiments, an antibody containing solution may be subjected to ultrafiltration (UF) and/or diafiltration (DF) 700 to concentrate the antibody. Ultrafiltration and/or diafiltration 700 may be performed in the absence or presence of a thiol containing additive.

Accordingly, one or more thiol containing additives may be used for one or more of the steps illustrated in FIG. 1. In some embodiments, additional or alternative purification steps may be included in an antibody purification process and one or more thiol-containing additives may be used in any or all of the purification steps. Also within the scope of the present disclosure are methods comprising a single or a few purification steps (e.g., only one or a subset of the steps illustrated in FIG. 1), for example one or a few chromatographic separation steps, each of which may be performed using one or more thiol containing additives. In some embodiments, methods comprise two chromatographic separations. In some embodiments, methods comprise three chromatographic separations. In some embodiments, methods comprise four chromatographic separations. In some embodiments, a thiol containing additive is only added to the antibody containing eluates from one or more chromatographic columns.

It should be appreciated that the order in which the chromatographic separations are performed is not limiting. For example, with reference to FIG. 1, ion exchange chromatography 400 may be performed prior to affinity chromatography 200, or hydrophobic interaction chromatography 500 may be performed prior to ion exchange chromatography 400.

Chromatography

In some embodiments, a thiol containing additive may be included after (and/or during) one or more chromatography steps used to separate an antibody from other components (e.g., host cell components) that are present in an antibody mixture (e.g., antibody sample).

In some embodiments, chromatographic separation comprises affinity chromatography. Examples of affinity chromatography include, but are not limited to, Protein A chromatography, Protein G chromatography, metal binding chromatography (e.g., nickel chromatography), lectin chromatography, and GST chromatography.

In some embodiments, chromatographic separation comprises ion exchange chromatography. Examples of anion exchange chromatography (AEX) include, but are not limited to, diethylaminoethyl (DEAE) chromatography, quaternary aminoethyl (QAE) chromatography, and quaternary amine(Q) chromatography. Examples of cation exchange chromatography include, but are not limited to, carboxymethyl (CM) chromatography, sulfoethyl (SE) chromatography, sulfopropyl (SP) chromatography, phosphate (P) chromatography, and sulfonate (S) chromatography.

In some embodiments, chromatographic separation comprises hydrophobic interaction chromatography (HIC). Examples of hydrophobic interaction chromatography include, but are not limited to, Phenyl Sepharose chromatography, Butyl Sepharose chromatography, Octyl Sepharose chromatography, Capto Phenyl chromatography, Toyopearl Butyl chromatography, Toyopearl Phenyl chromatography, Toyopearl Hexyl chromatography, Toyopearl Ether chromatography, and Toyopearl PPG chromatography.

In some embodiments, chromatographic separation comprises mixed mode chromatography. Mixed mode chromatography involves at least two types of chromatography, for example, affinity chromatography and ion exchange chromatography. Examples of mixed mode chromatography include, but are not limited to, MEP Hypercel chromatography, Capto-MMC chromatography, Capto-Adhere chromatography, Capto-Q chromatography, Capto-S chromatography, and ABx chromatography.

In some embodiments, chromatographic separations performed in accordance with the present application involve antibody samples and/or solutions having a pH between 3 to 9. In some embodiments, an antibody sample (e.g., a cell culture lysate comprising an antibody) has a pH between 3 to 9, In some embodiments, an antibody sample has a pH between 3.5 to 9, between 4 to 9, between 4.5 to 9, between 5 to 9, between 5.5 to 9, between 6 to 9, between 6.5 to 9, between 7 to 9, between 7.5 to 9, between 8 to 9, or between 8.5 to 9. In some embodiments, an antibody sample has a pH between 3 to 8.5, between 3 to 8, between 3 to 7.5, between 3 to 7, between 3 to 6.5, between 3 to 6, between 3 to 5.5, between 3 to 5, between 3 to 4.5, between 3 to 4, or between 3 to 3.5.

In some embodiments, an antibody mixture (e.g., an antibody mixture from a cell lysate) has a pH between 3 to 9. In some embodiments, an antibody mixture has a pH between 3.5 to 9, between 4 to 9, between 4.5 to 9, between 5 to 9, between 5.5 to 9, between 6 to 9, between 6.5 to 9, between 7 to 9, between 7.5 to 9, between 8 to 9, or between 8.5 to 9. In some embodiments, an antibody mixture has a pH between 3 to 8.5, between 3 to 8, between 3 to 7.5, between 3 to 7, between 3 to 6.5, between 3 to 6, between 3 to 5.5, between 3 to 5, between 3 to 4.5, between 3 to 4, or between 3 to 3.5.

In some embodiments, a solution (e.g., a loading solution, a wash solution, an elution solution) has a pH between 3 to 9. In some embodiments, a solution has a pH between 3.5 to 9, between 4 to 9, between 4.5 to 9, between 5 to 9, between 5.5 to 9, between 6 to 9, between 6.5 to 9, between 7 to 9, between 7.5 to 9, between 8 to 9, or between 8.5 to 9. In some embodiments, a solution has a pH between 3 to 8.5, between 3 to 8, between 3 to 7.5, between 3 to 7, between 3 to 6.5, between 3 to 6, between 3 to 5.5, between 3 to 5, between 3 to 4.5, between 3 to 4, or between 3 to 3.5.

In some embodiments, chromatographic separations performed in accordance with the present application may involve one or more loading solutions having a pH greater than the loading solution of a conventional chromatographic separation. For example, in some embodiments the pH of a loading solution comprising an antibody (e.g., along with a thiol containing additive) is adjusted to a pH of between 6 to 9 prior to contacting the loading solution with an anion exchange chromatography resin. In some embodiments, the pH of the loading solution contacted with an anion exchange chromatography resin is between 6 to 9. In some embodiments, the pH of the loading solution contacted with an anion exchange chromatography resin is between 6 to 6.5, between 6 to 7, between 6 to 7.5, between 6 to 8, or between 6 to 8.5. In some embodiments, the pH of the loading solution contacted with an anion exchange chromatography resin is between 6.5 to 9, between 7 to 9, between 7.5 to 9, between 8 to 9, or between 8.5 to 9. In some embodiments, the pH of the loading solution contacted with an anion exchange chromatography resin is at least 6, at least 6.5, at least 7 at least 7.5, at least 8, at least 8.5, and at least 9.

According to certain methods described herein, hydrophobic interaction chromatography may be performed at a pH of between 5 to 7. In some embodiments, the pH of a loading solution comprising an antibody (e.g., along with a thiol containing additive) is adjusted to a pH of between 5 to 7 prior to contacting the loading solution with a hydrophobic interaction chromatography resin. In some embodiments, the pH of the loading solution contacted with a hydrophobic interaction chromatography resin is between 5 to 7. In some embodiments, the pH of the loading solution contacted with a hydrophobic interaction chromatography resin is between 5 to 5.5, between 5 to 6, or between 5 to 6.5. In some embodiments, the pH of the loading solution contacted with a hydrophobic interaction chromatography resin is between 5.5 to 7, between 6 to 7, or between 6.5 to 7. In some embodiments, the pH of the loading solution contacted with a hydrophobic interaction chromatography resin is at least 5.5, at least 6, at least 6.5, and at least 7.

Chromatographic separations performed in accordance with the present application may involve one or more loading solutions comprising protein concentrations (e.g., antibody concentrations) greater than those in loading solutions of a conventional chromatographic separation. For example, a loading solution comprising a protein concentration (e.g., an antibody concentration) of at least 0.1 g/L, at least 10 g/L, or at least 100 g/L, or more may be contacted with a chromatography resin (e.g., an affinity chromatography resin or a hydrophobic interaction chromatography resin).

In some embodiments, the protein concentration of a loading solution contacted with a chromatography resin is between 0.1 g/L to 100 g/L. In some embodiments, the protein concentration of a loading solution contacted with a chromatography resin is between 0.1 g/L and 75 g/L, between OA g/L and 50 g/L, between 0.1 g/L and 2.5 g/L, between 0.1 g/L and 10 g/L, or between 0.1 g/L and 1 g/L. In some embodiments, the protein concentration of a loading solution contacted with a chromatography resin is between 1 g/L and 100 g/L, between 10 g/L and 100 g/L, between 25 g/L and 100 g/L, between 50 g/L and 100 g/L, or between 75 g/L and 100 g/L.

Chromatographic separations performed in accordance with the present application may involve a greater mass of protein loaded (e.g., mass of antibody loaded) per liter of chromatography resin compared to that of a conventional chromatographic separation. For example, the mass of protein loaded per liter of a chromatography resin may be at least 100 g/L, at least 1,000 g/L, at least 2,000 g/L, at least 10,000 g/L, at least 20,000 g/L or at least 30,000 g/L.

In some embodiments, the mass of protein loaded per liter of affinity chromatography resin is between 500 g/L to 2,000 g/L. In some embodiments, the mass of protein loaded per liter of an affinity chromatography resin is between 750 g/L and 2,000 g/L, between 1,000 g/L and 2,000 g/L, between 1250 g/L and 2,000 g/L, between 1,500 g/L and 2,000 g/L, or between 1,750 g/L, and 2,000 g/L. In some embodiments, the mass of protein loaded per liter of an affinity chromatography resin is between 500 g/L and 1,750 g/L, between 500 g/L and 1,500 g/L, between 500 g/L and 1,250 g/L, between 500 g/L and 1,000 g/L, or between 500 g/L and 750 g/L. In some embodiments, the mass of protein loaded per liter of an affinity chromatography resin is at least 500 g/L, at least 750 g/L, at least 1,000 g/L, at least 1,250 g/L, at least 1,500 g/L, at least 1,750 g/L, or at least 2,000 g/L.

In some embodiments, the mass of protein loaded per liter of hydrophobic interaction chromatography resin is between 200 g/L and 1,000 g/L. In some embodiments, the mass of protein loaded per liter of hydrophobic interaction chromatography resin is between 300 g/L and 1,000 g/L, between 400 g/L and 1,000 g/L, between 500 g/L and 1,000 g/L, between 600 g/L and 1,000 g/L, between 700 g/L and 1,000 g/L, between 800 g/L and 1,000 g/L, or between 900 g/L and 1,000 g/L. In some embodiments, the mass of protein loaded per liter of hydrophobic interaction chromatography resin is between 200 g/L and 900 g/L, between 200 g/L, and 800 g/L, between 200 g/L and 700 g/L, between 200 g/L, and 600 g/L, between 200 g/L and 500 g/L, between 200 g/L and 400 g/L, or between 200 g/L and 300 g/L. In some embodiments, the mass of protein loaded per liter of hydrophobic interaction chromatography resin is at least 200 g/L, at least 300 g/L, at least 400 g/L, at least 500 g/L, at least 600 g/L, at least 700 g/L, at least 800 g/L, at least 900 g/L, or at least 1,000 g/L.

Chromatographic separations performed in accordance with the present disclosure may allow longer hold times than those in conventional chromatographic separations. Without wishing to be bound by theory, it is believed that antibodies in the presence of a thiol containing additive are more stable than antibodies in the absence of a thiol containing additive. As used herein, "hold time" refers to the average amount of time that an antibody spends between chromatography steps. In some embodiments, antibody containing solutions may be held between chromatography steps to allow several batches of antibodies to be processed using one type of chromatographic separation and combined prior to proceeding to a subsequent different type of chromatographic separation. In some embodiments, antibody containing solutions may be held after a chromatographic step in order to combine several batches of antibody containing solution for an intermediate step such as a viral inactivation, filtration, and/or concentration step. It should be appreciated that antibody containing solutions obtained at different steps in a purification procedure typically have different levels of antibody purity (e.g., different levels of host cell protein, nucleic acid, lipid, and/or other contamination).

In some embodiments, the hold time is between 12 hours and 96 hours. In some embodiments, the hold time is between 12 hours and 84 hours, between 12 hours and 72 hours, between 12 hours and 60 hours, between 12 hours and 48 hours, between 12 hours and 36 hours, or between 12 hours and 24 hours. In some embodiments, the hold time is between 24 hours and 96 hours, between 36 hours and 96 hours, between 48 hours and 96 hours, between 60 hours and 96 hours, between 72 hours and 96 hours, or between 84 hours and 96 hours.

In some embodiments, the hold time is at least 12 hours, at least 24 hours, at least 36 hours, at least 48 hours, at least 60 hours, at least 72 hours, at least 84 hours, at least 96 hours or more.

Chromatographic separations performed in accordance with the present disclosure may allow longer long-term storage times of an antibody sample than those of an antibody sample prepared in conventional chromatographic separations. In some embodiments, the long-term storage time is between 0 months and 36 months. In some embodiments, the long-term storage time is between 0 months and 30 months, between 0 months and 24 months, between 0 months and 18 months, between 0 months and 12 months, and between 0 months and 6 months. In some embodiments, the long-term storage time is between 6 months and 36 months, between 12 months and 36 months, between 18 months and 36 months, between 24 months and 36 months, and between 30 months and 36 months.

In some embodiments, the long-term storage time is at least 1 month, at least 2 months, at least 3 months, at least 4 months, at least 5 months, at least 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 24 months, at least 36 months, or more. In some embodiments, the long-term storage time is at least 1 year, at least 2 years, at least 3 years, at least 4 years, at least 5 years, or more.

Chromatographic separations performed in accordance with the present application may be performed at any temperature. In some embodiments, the temperature is between 0° C. and 40° C. In some embodiments, the temperature is between 0° C. and 35° C., between 0° C. and 30° C., between 0° C. and 25° C., between 0° C. and 20° C., between 0° C. and 15° C. between 0° C. and 10° C., and between 0° C. and 5° C. In some embodiments, the temperature is between 5° C. and 40° C., between 10° C. and 40° C., between 15° C. and 40° C. between 20° C. and 40° C., between 25° C. and 40° C., between 30° C. and 40° C., and between 35° C. and 40° C.

Thiol Containing Additives

According to methods described herein, high molecular weight (HMW) aggregates can be prevented or reduced during antibody purification by adding a thiol containing additive to one or more steps of the purification process. Examples of thiol containing additives include, but are not limited to, cysteine, L-cysteine, sulfur dioxide, hydrogen sulfide, bisulfite, and glutathione.

The thiol containing additive(s) may be added to one or more antibody containing solutions during purification according to methods described herein. In some embodiments, a thiol containing additive is added to an elution solution comprising antibody. In some embodiments, a thiol containing additive is added to a solution comprising an antibody, for example, a loading solution. In some embodiments, a thiol containing additive is added to a solution used during purification, for example, a wash solution or an elution solution. In some embodiments, a thiol containing additive is added to a chromatography resin, for example, by equilibrating the chromatography resin with the thiol containing additive.

According to methods described herein, thiol containing additive(s) may be added to a solution at a final concentration of between 0.01 mM and about 1 mM, for example between 0.1 mM and about 1 mM, or between 0.5 mM and about 1 mM. In some embodiments, a final concentration of thiol containing additive(s) is 0.025 mM to about 1 mM, 0.05 mM to about 1 mM, 0.075 mM to about 1 mM, 0.1 mM to about 1 mM, 0.25 mM to about 1 mM, 0.5 mM to about 1 mM, or 0.75 mM to about 1 mM. In some embodiments, a final concentration of thiol containing additive(s) is 0.01 mM to about 0.75 mM, 0.01 mM to about 0.5 mM, 0.01 mM to about 0.25 mM, 0.01 mM to about 0.1 mM, 0.01 mM to about 0.075 mM, 0.01 mM to about 0.05 mM, or 0.01 mM to about 0.025 mM. In some embodiments, a higher final concentration of thiol containing additive may be used, for example between about 1 mM and about 2 mM, or up to about 5 mM, or about 5 mM to about 10 mM. As used herein, "about" means a numeric value having a range of ±25% around the cited value.

In some embodiments, thiol containing additive is glutathione. In some embodiments, glutathione may be added to a solution at a final concentration of between 0.01 mM and about 1 mM, for example between 0.1 mM and about 1 mM, or between 0.5 mM and about 1 mM. In some embodiments, a final concentration of glutathione is 0.025 mM to about 1 mM, 0.05 mM to about 1 mM, 0.075 mM to about 1 mM, 0.1 mM to about 1 mM, 0.25 mM to about 1 mM, 0.5 mM to about 1 mM, or 0.75 mM to about 1 mM. In some embodiments, a final concentration of glutathione is 0.01 mM to about 0.75 mM, 0.01 mM to about 0.5 mM, 0.01 mM to about 0.25 mM, 0.01 mM to about 0.1 mM, 0.01 mM to about 0.075 mM, 0.01 mM to about 0.05 mM, or 0.01 mM to about 0.025 mM. In some embodiments, a higher final concentration of glutathione may be used, for example between about 1 mM and about 2 mM, or up to about 5 mM, or about 5 mM to about 10 mM.

A thiol containing additive may be provided in its reduced form (e.g., GSH) or as a combination of the reduced form (e.g., GSH) and oxidized form (e.g., GSSG). For example, thiol containing additive may be provided as GSH alone or as GSH in combination with GSSG. In another example, a thiol containing additive may be provided as cysteine alone or as cysteine in combination with cystine.

According to methods described herein, thiol containing additive(s) may be added to a solution at various ratios of the reduced form to the oxidized form. In some embodiments, the ratio of reduced thiol containing additive to oxidized thiol containing additive is about 1:1, about 2:1, about 3:1, about 4:1, about 5:1, about 6:1, about 7:1, about 8:1, about 9:1, or about 10:1. In some embodiments, the ratio of reduced thiol containing additive to oxidized thiol containing additive is about 1:2, about 1:3, about 1:4, about 1:5, about 1:6, about 1:7, about 1:8, about 1:9, or about 1:10. In some embodiments, the ratio of GSH to GSSG is about 1:1, about 2:1, about 3:1, about 4:1, about 5:1, about 6:1, about 7:1, about 8:1, about 9:1, or about 10:1. In some embodiments, the ratio of GSH to GSSG is about 1:2, about 1:3, about 1:4, about 1:5, about 1:6, about 1:7, about 1:8, about 1:9, or about 1:10.

In some embodiments, a concentrated solution of a thiol containing additive is spiked into an antibody mixture (e.g., antibody sample) and/or a solution (e.g., a loading solution, a wash solution, an elution solution). As used herein, "spiking" refers to adding an amount of a concentrated thiol containing additive solution (e.g., a stock solution) into an antibody containing solution to obtain a desired final concentration of thiol containing additive in the antibody containing solution. In some embodiments, a stock solution is spiked into an antibody solution at a ratio of 1:10, 1:50, 1:100, 1:500, or 1:1000.

According to methods described herein, thiol containing additive(s) may be added to a solution having a pH between 3 to 9. In some embodiments, thiol containing additive(s) may be added to an elution solution having a pH between 3 to 9. In some embodiments, thiol containing additive(s) may be added to an elution solution having a pH between 3 to 8.5, between 3 to 8, between 3 to 7.5, between 3 to 7, between 3 to 6.5, between 3 to 6, between 3 to 5.5, between 3 to 4.5, between 3 to 4, or between 3 to 3.5. In some embodiments, thiol containing additive(s) may be added to an elution solution having a pH between 3.5 to 9, between 4 to 9, between 4.5 to 9, between 5 to 9, between 5.5 to 9, between 6 to 9, between 6.5 to 9, between 7 to 9, between 7.5 to 9, between 8 to 9, or between 8.5 to 9.

The thiol containing additive may be used at a constant concentration or variable concentrations during antibody purification. In some embodiments, thiol containing additive is added at a constant concentration. For example, thiol containing additive is added at a constant concentration to an elution from two or more chromatographic separations.

In some embodiments, variable concentrations of thiol containing additive are used during one purification step. For example, a first solution (e.g., a wash solution) comprising a thiol containing additive can be contacted with a chromatography resin and a second solution (e.g., an elution solution) comprising an increased amount of the thiol containing additive can then be contacted with the chromatography resin.

In some embodiments, variable concentrations of thiol containing additive are used during two or more purification steps. For example, a first concentration of a thiol containing additive may be added to an elution solution from a first chromatography step and a second concentration of a thiol containing additive that differs from the first concentration (e.g., greater than or less than) may be added to an elution solution from a second chromatography step. In some embodiments, thiol containing additive may be added at increasing concentrations (e.g., a step-wise gradient of increasing thiol containing additive concentrations). In some embodiments, thiol containing additive may be added at decreasing concentrations (e.g., a step-wise gradient of decreasing thiol containing additive concentrations).

It is also within the scope of the present disclosure to use more than one thiol containing additive during antibody purification. For example, a first thiol containing additive (e.g., glutathione) may be added during a chromatographic separation (e.g., affinity chromatography) and a second thiol containing additive (e.g., cysteine) may be added during another purification step (e.g., viral filtration). In another example, a first thiol containing additive (e.g., glutathione) may be used during a first chromatographic separation (e.g., affinity chromatography) and a second thiol containing additive (e.g., cysteine) may be used during a second chromatographic separation (e.g., anion exchange chromatography).

High Molecular Weight (HMW) Aggregates

According to methods described herein, high molecular weight (HMW) aggregates may be measured before, at substantially the same time as, or after, the addition of a thiol containing additive. As used herein, the term "aggregates" refers to aggregates of an antibody which include dimers, trimers, tetramers or high molecular weight (HMW) aggregates comprising any number of antibody monomers aggregated into a high molecular weight aggregate.

Without wishing to be bound by theory, HMW aggregates may be formed when two or more antibodies are joined via non-covalent interactions and/or covalent interactions. For example, HMW aggregates may be formed via non-covalent protein-protein interactions between two or more antibodies. In another example, HMW aggregates may be formed aria covalent interactions such as reducible covalent interactions (e.g., disulfide mediated interactions) and/or non-reducible covalent interactions (e.g., carbonyl mediated interactions). In yet another example, HMW aggregates may be formed via non-covalent interactions and covalent interactions. Thus, disrupting non-covalent interactions and/or covalent interactions that mediate HMW aggregation formation will, in theory, minimize formation of such aggregates. An example of a technique for disrupting aggregate forming interactions using the thiol containing additive (e.g., glutathione) is shown in Table 1. These techniques are in no way limiting as other techniques may be used to disrupt aggregate formation.

TABLE 1

Techniques for disrupting aggregate forming interactions.

| Interaction | Technique | Non-Limiting Example Reaction |
|---|---|---|
| Non-covalent | Block free thiol | RSH + GSH ⇌ R—S—SG + 2 H+ + 2 e− |
| Reducible Covalent | Dissociate dimers and | A-ss-B + GSH -----> A-ss-GSH + B-SH |
| | Disulfide exchange | A-ss-GSH + GSH -----> A-SH + GSSG |

TABLE 1-continued

Techniques for disrupting aggregate forming interactions.

| Interaction | Technique | Non-Limiting Example Reaction |
|---|---|---|
| Non-Reducible Covalent | Block carbonyls | GSH + R—CH═CH—COR -----> R—CH(SG)-CH2—COR |

In some embodiments, the presence of HMW aggregates is evaluated at least once a day during antibody purification. In some embodiments, the presence of HMW aggregates is evaluated at least once a day during antibody storage. In some embodiments, methods described herein result in a reduced level of about 0.5%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, or 90% of % HMW aggregates compared to purifications performed in the absence of a thiol containing additive.

Any method for detecting protein aggregates may be used in accordance with methods disclosed herein. Methods for detecting protein aggregates include, but are not limited to, native polyacrylamide gel electrophoresis (PAGE), sodium dodecyl sulfate-polyacrylamide gel electrophoresis (SDS-PAGE), capillary gel electrophoresis (CGE), size exclusion chromatography (SEC), analytical ultracentrifugation (AUC), field flow fractionation (FFF), light scattering detection, sedimentation velocity, UV spectroscopy, differential scanning calorimetry, turbidimetry, nephelometry, microscopy, size exclusion chromatography-high performance liquid chromatography (SEC-HPLC), reverse phase-high performance liquid chromatography (RP-HPLC), electrospray ionization tandem mass spectroscopy (ESI-MS), tandem RP-HPLC/ESI-MS, or a combination thereof.

Antibodies

Methods disclosed herein (e.g., using one or more thiol containing additives) may be used to purify antibodies or fragments thereof. Examples of antibodies include, but are not limited to, monoclonal antibodies, chimeric antibodies, non-human antibodies, human antibodies, and humanized antibodies.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')$_2$, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody can be an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

Antibodies purified according to methods described herein can be murine, rat, human, or of any other origin (including chimeric or humanized antibodies). In some examples, the antibody comprises a modified constant region, such as a constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in Eur. J. Immunol. (1999) 29:2613-2624; PCT Application No. PCT/GB99/01441; and/or UK Patent Application No. 9809951.8.

Any of the antibodies purified according to methods described herein can be either monoclonal (Mab) or polyclonal. A "monoclonal antibody" refers to a homogenous antibody population and a "polyclonal antibody" refers to a heterogenous antibody population. These two terms do not limit the source of an antibody or the manner in which it is made. In some embodiments, a monoclonal antibody is expressed from a recombinant nucleic acid (e.g., a plasmid) in a host cell.

In some embodiments, the antibody purified according to methods described herein is a humanized antibody. Humanized antibodies refer to forms of non-human antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody, in some embodiments, also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation.

In some embodiments, the antibody purified according to methods described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in one or more variable and/or constant regions.

In some embodiments, the antibody disclosed herein specifically binds a target antigen, such as human α-synuclein. An antibody that "specifically binds" (used interchangeably herein) to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically (or preferentially) binds to an α-synuclein epitope is an antibody that binds this α-synuclein epitope with greater affinity, avidity, more readily, and/or with greater duration than it binds to other α-synuclein epitopes or non-α-synuclein epitopes. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

In some embodiments, a thiol containing additive can be used in one or more steps of a purification procedure for one or more of the following non-limiting antibodies: 3F8, 8H9, abagovomab, abciximab, actoxumab, adalimumab, adecatumumab, aducanumab, afelimomab, afutuzumab, alacizumab pegol, ALD, alemtuzumab, alirocumab, altumomab pentetate, amatuximab, anatumomab mafenatox, anifrolumab, anrukinzumab (or IMA-638), apolizumab, arcitumomab, aselizumab, atinumab, atlizumab (or tocilizumab), atorolimumab, bapineuzumab, basiliximab, bavituximab, bectumomab, belimumab, benralizumab, bertilimumab, besilesomab, bevacizumab, bezlotoxumab, biciromab, bimagrumab, bivatuzumab mertansine, blinatumomab, blosozumab, brentuximab vedotin, briakinumab, brodalumab, canakinumab, cantuzumab mertansine, cantuzumab ravtansine, caplacizumab, capromab pendetide, carlumab, catumaxomab, cBR-doxorubicin immunoconjugate, cedelizumab, certolizumab pegol, cetuximab, citatuzumab bogatox, cixutumumab, clazakizumab, clenoliximab, clivatuzumab tetraxetan, conatumumab, concizumab, crenezumab, dacetuzumab, daclizumab, dalotuzumab, daratumumab, demcizumab, denosumab, detumomab, dorlimomab aritox, drozitumab, duligotumab, dupilumab, dusigitumab, ecromeximab, eculizumab, edobacomab, edrecolomab, efalizumab, efungumab, eldelumab, elotuzumab, elsilimomab, enavatuzumab, enlimomab pegol, enokizumab, enoticumab, ensituximab, epitumomab cituxetan, epratuzumab, erlizumab, ertumaxomab, etaracizumab, etrolizumab, evolocumab, exbivirumab, fanolesomab, faralimomab, farletuzumab, fasinumab, FBTA, felvizumab, fezakinumab, ficlatuzumab, figitumumab, flanvotumab, fontolizumab, foralumab, foravirumab, fresolimumab, fulranumab, futuximab, galiximab, ganitumab, gantenerumab, gavilimomab, gemtuzumab ozogamicin, gevokizumab, girentuximab, glembatumumab vedotin, golimumab, gomiliximab, guselkumab, ibalizumab, ibritumomab tiuxetan, icrucumab, igovomab, IMAB, imciromab, imgatuzumab, inclacumab, indatuximab ravtansine, infliximab, intetumumab, inolimomab, inotuzumab ozogamicin, ipilimumab, iratumumab, itolizumab, ixekizumab, keliximab, labetuzumab, lambrolizumab, lampalizumab, lebrikizumab, lemalesomab, lerdelimumab, lexatumumab, libivirumab, ligelizumab, lintuzumab, lirilumab, lodelcizumab, lorvotuzumab mertansine, lucatumumab, lumiliximab, mapatumumab, margetuximab, maslimomab, mavrilimumab, matuzumab, mepolizumab, metelimumab, milatuzumab, minretumomab, mitumomab, mogamulizumab, morolimumab, motavizumab, moxetumomab pasudotox, muromonab-CD, nacolomab tafenatox, namilumab, naptumomab estafenatox, narnatumab, natalizumab, nebacumab, necitumumab, nerelimomab, nesvacumab, nimotuzumab, nivolumab, nofetumomab merpentan, ocaratuzumab, ocrelizumab, odulimomab, ofatumumab, olaratumab, olokizumab, omalizumab, onartuzumab, ontuxizumab, oportuzumab monatox, oregovomab, orticumab, otelixizumab, otlertuzumab, oxelumab, ozanezumab, ozoralizumab, pagibaximab, palivizumab, panitumumab, panobacumab, parsatuzumab, pascolizumab, pateclizumab, patritumab, pemtumomab, perakizumab, pertuzumab, pexelizumab, pidilizumab, pinatuzumab vedotin, pintumomab, placulumab, polatuzumab vedotin, ponezumab, priliximab, pritoxaximab, pritumumab, PRO 140, quilizumab, racotumomab, radretumab, rafivirumab, ramucirumab, ranibizumab, raxibacumab, regavirumab, reslizumab, rilotumumab, rituximab, robatumumab, roledumab, romosozumab, rontalizumab, rovelizumab, rupalizumab, samalizumab, sarilumab, satumomab pendetide, secukinumab, seribantumab, setoxaximab, sevirumab, sibrotuzumab, SGN-CD19A, SGN-CD33A, sifalimumab, siltuximab, simtuzumab, siplizumab, sirukumab, solanezumab, solitomab, sonepcizumab, sontuzumab, stamulumab, sulesomab, suvizumab, tabalumab, tacatuzumab tetraxetan, tadocizumab, talizumab, tanezumab, taplitumomab paptox, tefibazumab, telimomab aritox, tenatumomab, teneliximab, teplizumab, teprotumumab, TGN, ticilimumab (or tremelimumab), tildrakizumab, tigatuzumab, TNX-650, tocilizumab (or atlizumab), toralizumab, tositumomab, tovetumab, tralokinumab, trastuzumab, TRBS, tregalizumab, tremelimumab, tucotuzumab celmoleukin, tuvirumab, ublituximab, urelumab, urtoxazumab, ustekinumab, vantictumab, vapaliximab, vatelizumab, vedolizumab, veltuzumab, vepalimomab, vesencumab, visilizumab, volociximab, vorsetuzumab mafodotin, votumumab, zalutumumab, zanolimumab, zatuximab, ziralimumab and zolimomab aritox.

In some embodiments, a thiol containing additive can be used in one or more steps of a purification procedure for one or more of the following proteins: anti-α-synuclein (e.g., BIIB054), anti-BDCA2 (e.g., BIIB059), anti-LINGO, anti-LINGO-1, interferon (e.g., interferon beta 1a-AVONEX), Abciximab (REOPRO®), Adalimumab (HUMIRA®), Aducanumab, Alemtuzumab (CAMPATH®), Basiliximab (SIMULECT®), Bevacizumab (AVASTIN®), Cetuximab (ERBITUX®), Certolizumab pegol (CIMZIA®), Daclizumab (ZENAPAX®), Eculizumab (SOLIRIS®), Efalizumab (RAPTIVA®), Gemtuzumab (MYLOTARG®), Ibritumomab tiuxetan (ZEVALIN®), Infliximab (REMICADE®), Muromonab-CD3 (ORTHOCLONE OKT3®), Natalizumab (TYSABRI®), Omalizumab (XOLAIR®), Palivizumab (SYNAGIS®), Panitumumab (VECTIBIX®), Ranibizumab (LUCENTIS®), Rituximab (RITUXAN®), Tositumomab (BEXXAR®), and/or Trastuzumab (HERCEPTIN®). In some embodiments, the protein is Aducanumab. In some embodiments, the protein is Natalizumab (TYSABRI®). In some embodiments, the protein is a blood cascade protein. Blood cascade proteins are known in the art and include, but are not limited to, Factor VII, tissue factor, Factor IX, Factor X, Factor XI, Factor XII, Tissue factor pathway inhibitor, Factor V, prothrombin, thrombin, vonWillebrandFactor, kininigen, prekallikrien, kallikrein, fribronogen, fibrin, protein C, thrombomodulin, and antithrombin. In some embodiments, the blood cascade protein is Factor IX or Factor VIII.

Cell Culture

Antibodies may be produced in cell cultures using methods known in the art. Antibodies produced in cell culture may be recombinant antibodies (e.g., expressed from a recombinant nucleic acid, for example a plasmid) or antibodies endogenously expressed by the cells grown in culture.

Cell cultures may comprise, for example, bacterial cells, yeast cells, or mammalian cells. Examples of mammalian cells suitable for producing antibodies to be purified according to methods described herein include, but are not limited to, CHO (Chinese Hamster Ovary) (including CHO-K1, CHO DG44, and CHO DUXB1 1), VERO, HeLa, (human cervical carcinoma), CVI (monkey kidney line), (including COS and COS-7), BHK (baby hamster kidney), MDCK, CI 27, PC 12, HEK-293 (including HEK-293T and HEK-293E), PER C6, NSO, WI38, R1610 (Chinese hamster fibroblast) BALBC/3T3 (mouse fibroblast), HAK (hamster kidney line), SP2/0 (mouse myeloma), P3x63-Ag3.653 (mouse myeloma), BFA-1c1BPT (bovine endothelial cells), RAJI (human lymphocyte) and 293 (human kidney) cells. In some embodiments, the cells are CHO cells or a derivative thereof.

Cell culture media may vary according to the type of cell being cultured. In some embodiments, the cell culture media is a commercially available media. In some embodiments, the cell culture media comprises inorganic salts, carbohydrates (e.g., sugars such as glucose, galactose, maltose or fructose), amino acids, vitamins (e.g., B group vitamins (e.g., B12), vitamin A vitamin E, riboflavin, thiamine and biotin), fatty acids and lipids (e.g., cholesterol and steroids), proteins and peptides (e.g., albumin, transferrin, fibronectin and fetuin), serum (e.g., compositions comprising albumins, growth factors and growth inhibitors, such as, fetal bovine serum, newborn calf serum and horse serum), trace elements (e.g., zinc, copper, selenium and tricarboxylic acid intermediates), hydrolysates (hydrolyzed proteins derived from plant or animal sources), or a combination thereof. Examples of cell culture media include, but are not limited to, basal media (e.g., MEM, DMEM, GMEM), complex media (RPMI 1640, Iscoves DMEM, Leibovitz L-15, Leibovitz L-15, TC 100), and serum free media (e.g., CHO, Ham F10 and derivatives, Ham F12, DMEM/F12). In some embodiments, the cell culture media comprises a buffer (e.g., PBS, Hanks BSS, Earles salts, DPBS, HBSS, and EBSS).

In some aspects, cell cultures are conducted in a bioreactor. A bioreactor refers to a vessel, including an open or closed vessel, for culturing one or more cells or organisms, or for maintaining or producing cellular components, including recombinant proteins. In some embodiments, a bioreactor is used for the production of a therapeutic protein (e.g., a recombinant protein, such as an antibody) by cultured cells. In some embodiments, bioreactors are made of corrosion resistant alloys, such as stainless steel (e.g., grade-316L stainless steel). However, in some embodiments, a bioreactor may be made of glass, ceramics, plastic, or any number of materials or combinations thereof. In some embodiments, a bioreactor is configured with one or more supply lines for supplying nutrients, glucose, $O_2$, $CO_2$, and other components to the bioreactor. In some embodiments, a bioreactor is configured with one or more output lines for removing waste or other components from the bioreactors. In some embodiments, a bioreactor is configured with one or more spargers for bubbling a gas (e.g., $O_2$, $CO_2$) through a culture medium. In some embodiments, a bioreactor comprises one or more agitators or mixers for mixing a culture medium. In some embodiments, a bioreactor comprises one or more heating elements and one or more thermocouples configured to permit the temperature of the bioreactor culture to be controlling.

In some embodiments, a bioreactor has a working volume (e.g., of culture medium) of at least 0.5 L, at least 1 L, at least 10 L, at least 100 L, at least 250 L, at least 500 L, at least 500 L, at least 1000 L, at least 2000 L, at least 3000 L, at least 4000 L, at least 5000 L, at least 7500 L, at least 10000 L, at least 12500 L, at least 15000 L, at least 20000 L, at least 100000 L, or more. In some embodiments, a bioreactor has a working volume in a range of 0.5 L to 10 L, 0.5 L to 100 L, 0.5 L to 500 L, 500 L to 1000 L, 500 L to 2500 L, 500 L to 5000 L, 500 L to 10000 L, 500 L to 15000 L, 500 L to 20000 L, 1000 L to 4000 L, 500 L to 100000 L, 2000 L to 5000 L, 2000 L to 10000 L, 2000 L to 15000 L, 2000 L to 20000 L, 2000 L to 100000 L, 15000 L to 20000 L, 15000 L to 100000 L, 20000 L to 50000 L, 20000 L to 100000 L, or 50000 L to 100000 L. In some embodiments, a bioreactor comprises a culture that produces or is capable of producing at least 1 gram, at least 10 grams, at least 100 grams, 500 grams, 1000 grams, 2000 grams, 3000 grams, or more of a recombinant protein (e.g., a recombinant antibody). In some embodiments, a bioreactor culture produces or is capable of producing 1 gram to 10 grams, 1 gram to 100 grams, 1 gram to 500 grams, 10 gram to 1000 grams, 10 grams to 2000 grams, 100 grams to 1000 grams, 500 grams to 5000 grams, or more of a recombinant protein (e.g., a recombinant antibody).

Methods of Use

Methods of the present disclosure may also be used to isolate an antibody that can be mixed with a pharmaceutically acceptable carrier (excipient), including buffer, to form a pharmaceutical composition for use in treating a subject.

As used herein, "acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover. In one example, a pharmaceutical composition described herein contains two or more antibodies purified according to methods provided herein that recognize different epitopes of the target antigen. In another example, the pharmaceutical composition comprises at least one antibody purified according to methods provided herein and at least one other additional medicament (e.g., one antibody and one small molecule).

An effective amount of the pharmaceutical composition comprising an antibody purified according to methods disclosed herein may be administered to a subject (e.g., a human) in need of the treatment via a suitable route (e.g., intravenous administration). The subject to be treated can be a mammal, for example a human. Other mammals include, but are not limited to, farm animals, sport animals, pets, primates, horses, dogs, cats, mice and rats.

Conventional methods, known to those of ordinary skill in the art of medicine, can be used to administer the pharmaceutical composition to the subject, depending upon the type of disease to be treated or the site of the disease. In some embodiments, the composition can be administered intravascularly (IV). The composition also can be administered via other conventional routes, e.g., administered orally, parenterally, by inhalation spray, topically, rectally, nasally, buccally, vaginally or via an implanted reservoir.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation.

As used herein, the term "treating" refers to the application or administration of a composition including one or more antibodies purified as described herein to a subject, who has a disease, a symptom of a disease, or a predisposition toward a disease, with the purpose to cure, heal, alleviate, relieve, alter, remedy, ameliorate, improve, or affect the disease, the symptom of the disease, or the predisposition toward the disease. A "disease" is any condition that would benefit from treatment with an antibody purified according to methods described herein.

Methods of the present disclosure may also be used to make an antibody that can be used for non-therapeutic uses (e.g., research purposes). In some embodiments, the antibodies purified as described herein may be used to study cell behavior and/or cell mechanisms (e.g., the discovery of novel biological pathways or processes). In some embodiments, the antibodies purified as described herein may be used to as probes in labeling and detection methods.

EXAMPLES

Example 1: Lower Percentages of High Molecular Weight (% HMW) Aggregates were Detected in Mab Samples Spiked with Glutathione Compared to Control, Un-Spiked, Mab Samples To evaluate the effects of glutathione on high molecular weight (HMW) aggregate formation, Mab eluates were spiked with glutathione and the % HMW formation was monitored over a three day time period. Eluates of Mab A, Mab B, and Mab C were evaluated at pH 5.7 and 7.1. A stock solution of 40 mM reduced glutathione and 20 mM oxidized glutathione was spiked at 1% v/v into the Mab eluates.

Figure 3A:
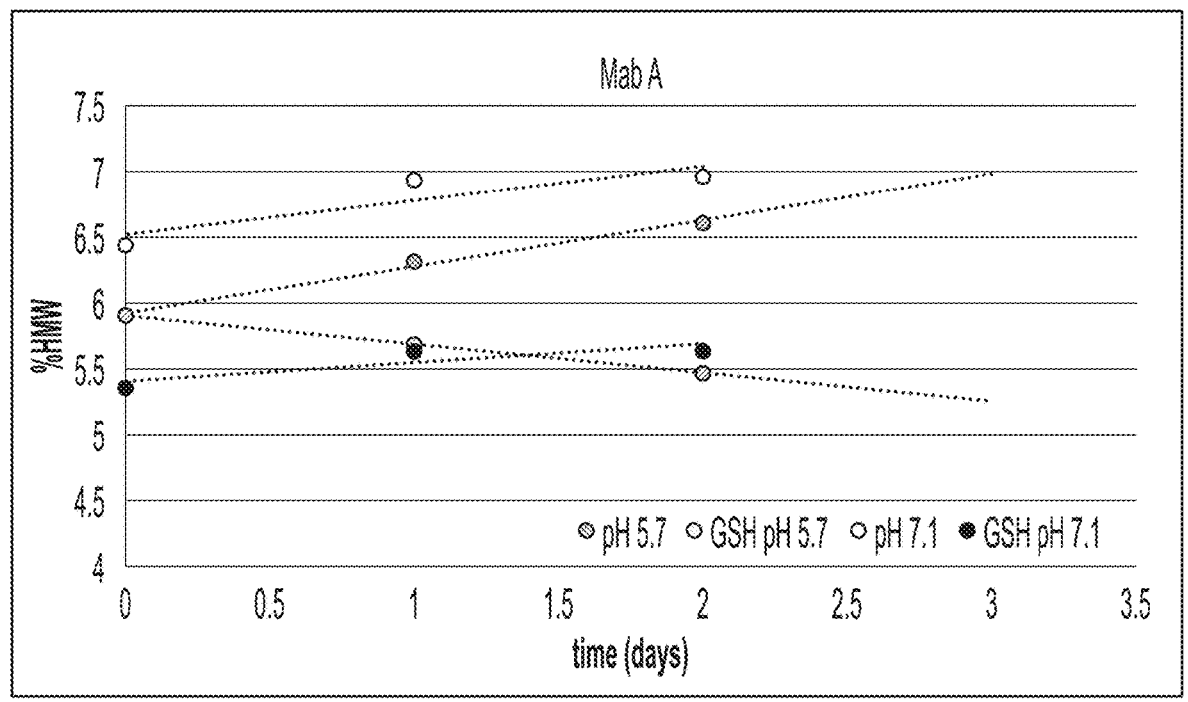
FIG. 3A is a graph showing the percentage of high molecular weight (HMW) aggregates detected in a solution comprising Mab A at pH 5.7 or 7.1 in the absence or presence of glutathione. The % HMW aggregates were detected on day 0, 1, 2 and 3.
Figure 3B:
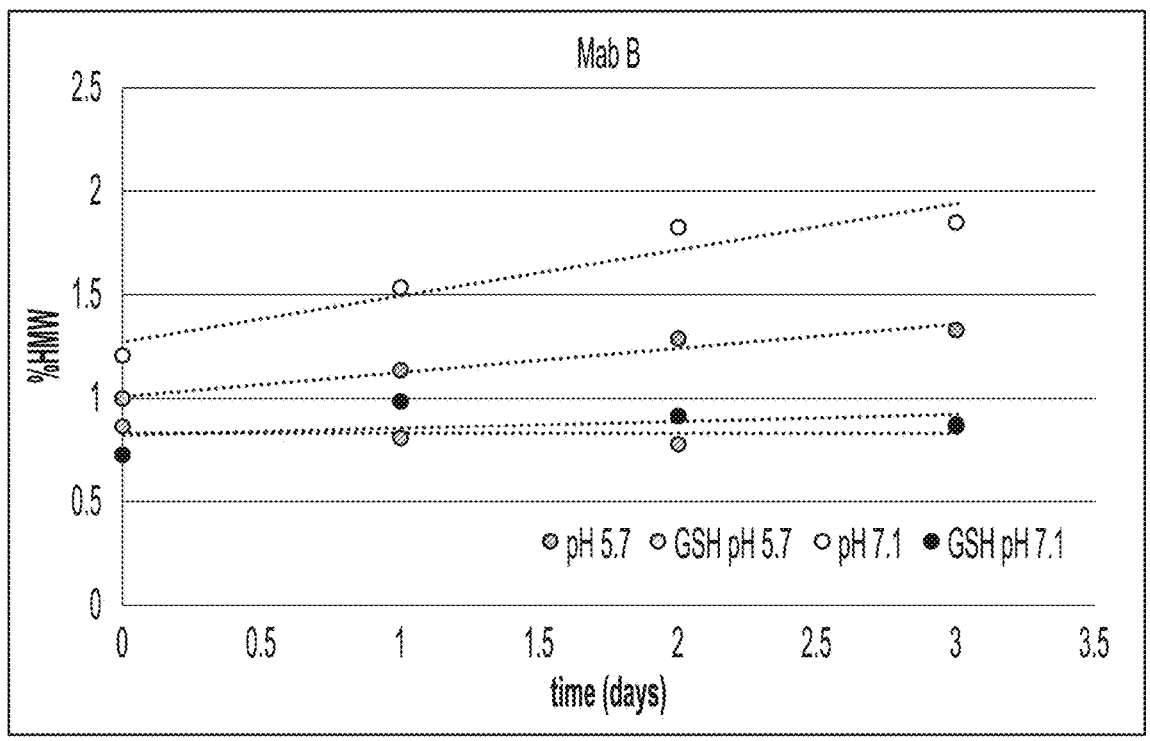
FIG. 3B is a graph showing the percentage of high molecular weight (HMW) aggregates detected in a solution comprising Mab B at pH 5.7 or 7.1 in the absence or presence of glutathione. The % HMW aggregates were detected on day 0, 1, 2 and 3.
Figure 3C:
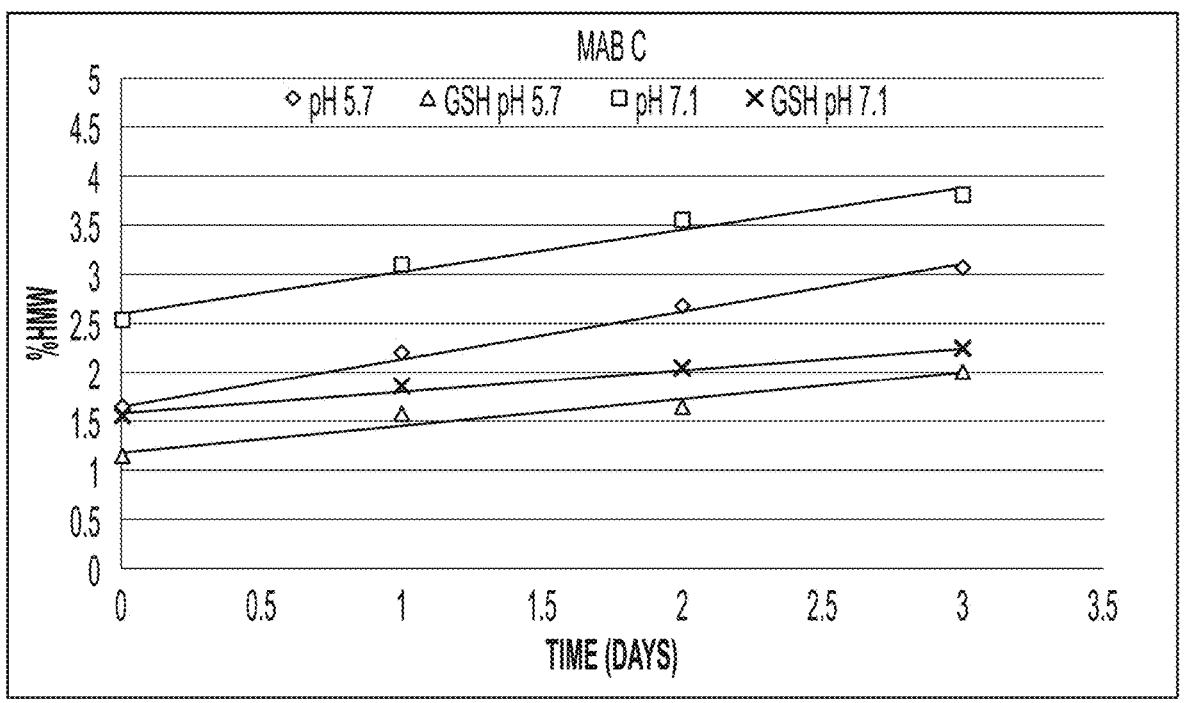
FIG. 3C is a graph showing the percentage of high molecular weight (HMW) aggregates detected in a solution comprising Mab C at pH 5.7 or 7.1 in the absence or presence of glutathione. The % HMW aggregates were detected on day 0, 1, 2 and 3.
Figure 4A:
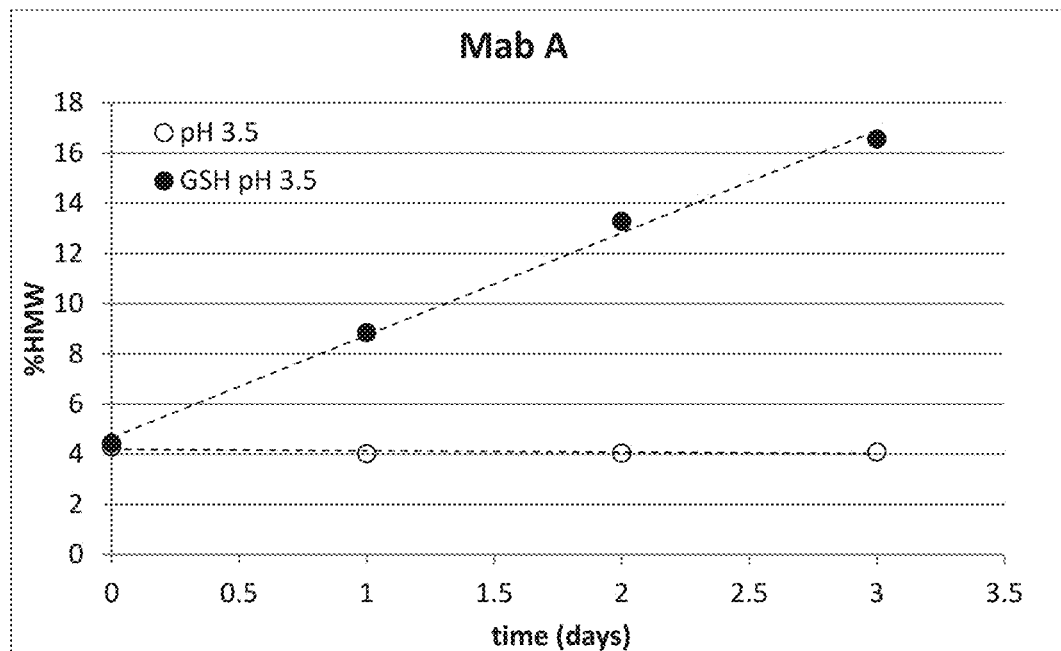
FIG. 4A is a graph showing the percentage of high molecular weight (HMW) aggregates detected in a solution comprising Mab A at pH 3.5 in the absence or presence of glutathione. The % HMW aggregates were detected on day 0, 1, 2 and 3.
Figure 4B:
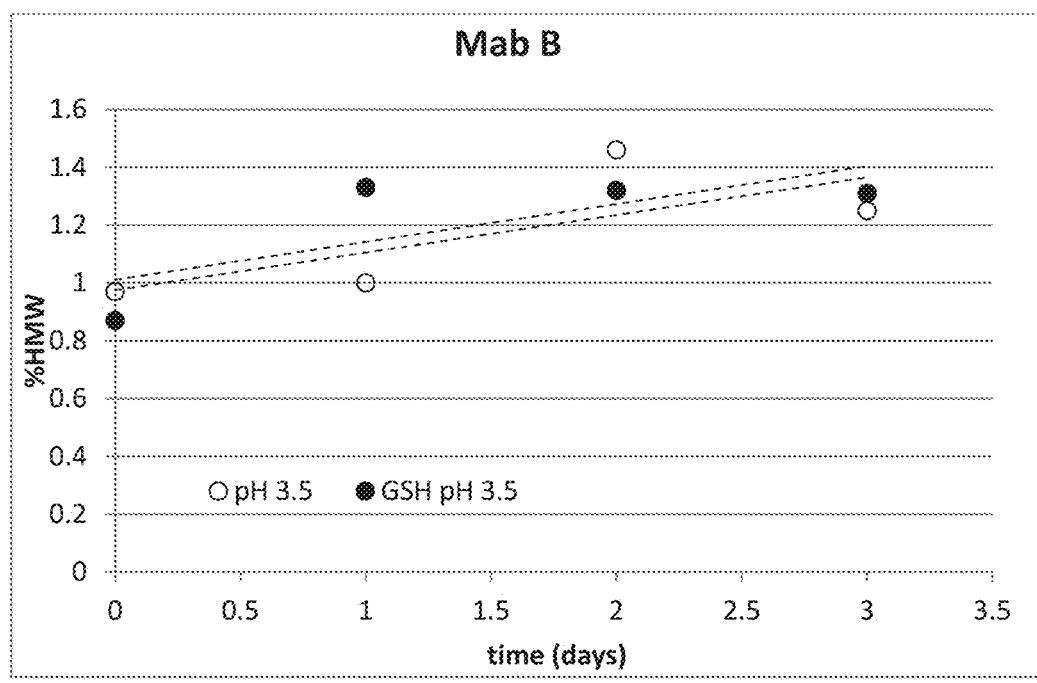
FIG. 4B is a graph showing the percentage of high molecular weight (HMW) aggregates detected in a solution comprising Mab B at pH 3.5 in the absence or presence of glutathione. The % HMW aggregates were detected on day 0, 1, 2 and 3.
Figure 4C:
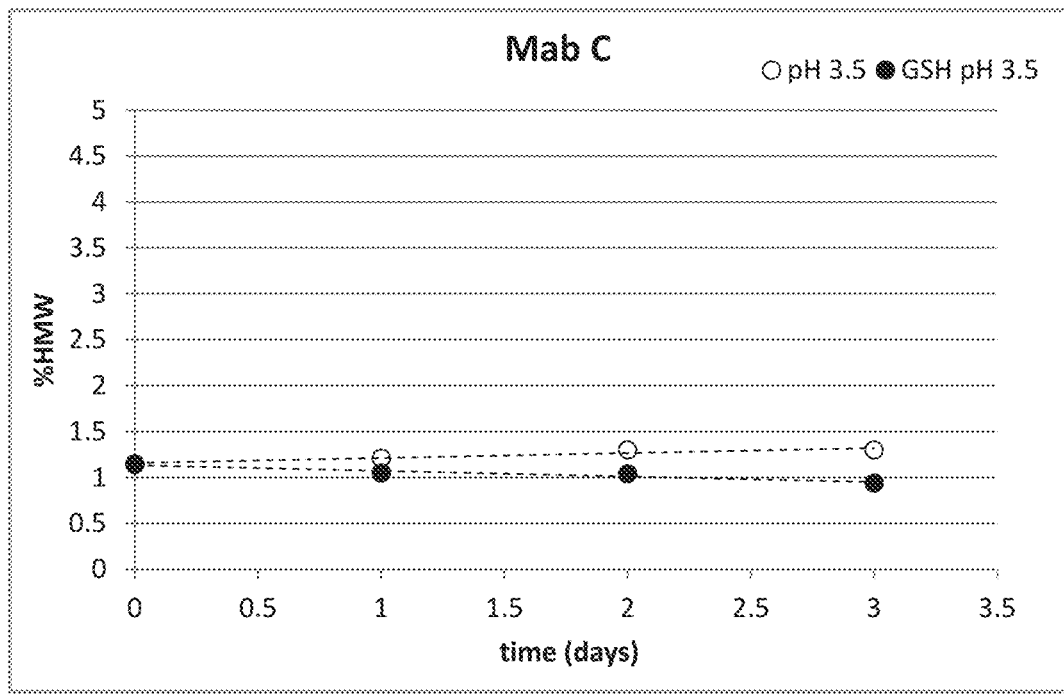
FIG. 4C is a graph showing the percentage of high molecular weight (HMW) aggregates detected in a solution comprising Mab C at pH 3.5 in the absence or presence of glutathione. The % HMW aggregates were detected on day 0, 1, 2 and 3.

For each Mab eluate at pH 5.7 and pH 7.1, the % HMW aggregates were reduced in the sample spiked with glutathione compared to a control, un-spiked, sample (FIGS. 3A-3C). The % HMW aggregate formation for Mab A-C at pH 3.5 was also determined. Minimal change in % HMW aggregate formation was observed for Mab B (FIG. 4B) and Mab C (FIG. 4C), however Mab A (FIG. 4A) showed an increased formation of % HMW.

Thus, Mab samples having a pH of 5.7 or greater had reduced % HMW aggregate formation compared to control, un-spiked, samples.

Figure 2:
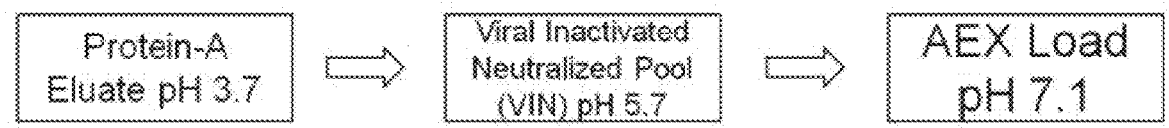
FIG. 2 is a flowchart of an exemplary method for purifying an antibody in which glutathione may be added at different steps during purification, in accordance with some embodiments of the technology described herein.

Example 2: Spiking Glutathione at Various Intermediates in the Mab Purification Process Minimized Formation of High Molecular Weight (HMW) Aggregates To evaluate the effects of glutathione on high molecular weight (HMW) aggregate formation during the initial purification steps shown in FIG. 2, glutathione was spiked at different steps and % HMW formation was detected. For example, glutathione was spiked into the Mab Eluate, and into the viral inactivation and neutralization (VIN) pool, and % HMW formation was detected throughout purification. Mab eluates of Mab B and Mab C, and VIN pool of Mab A were spiked 1% v/v with a stock solution of 40 mM reduced glutathione and 20 mM oxidized glutathione.

Figure 5:
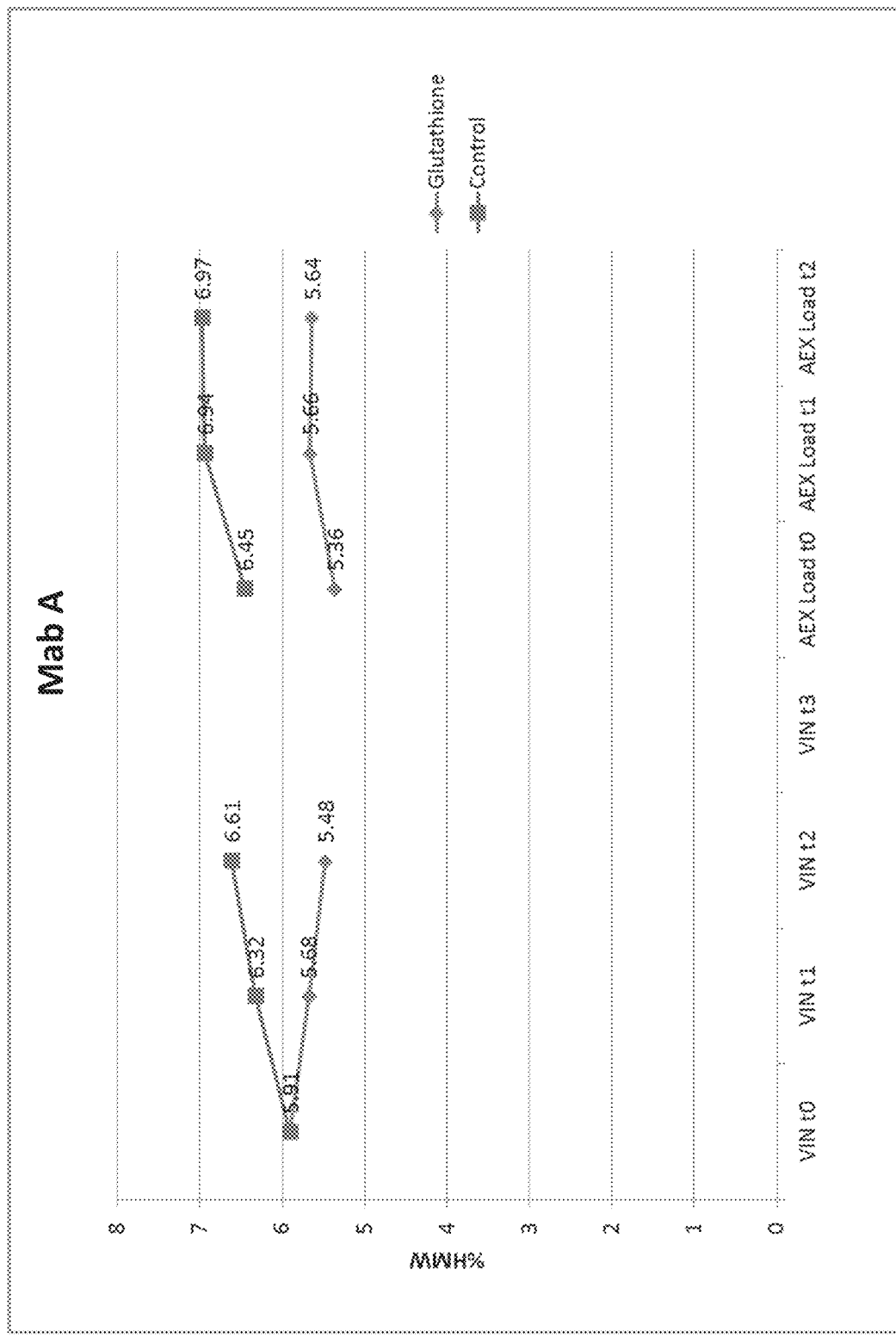
FIG. 5 is a graph showing the percentage of high molecular weight (MHW) aggregates detected in a solution comprising Mab A during an exemplary purification as shown in FIG. 2.
Figure 6:
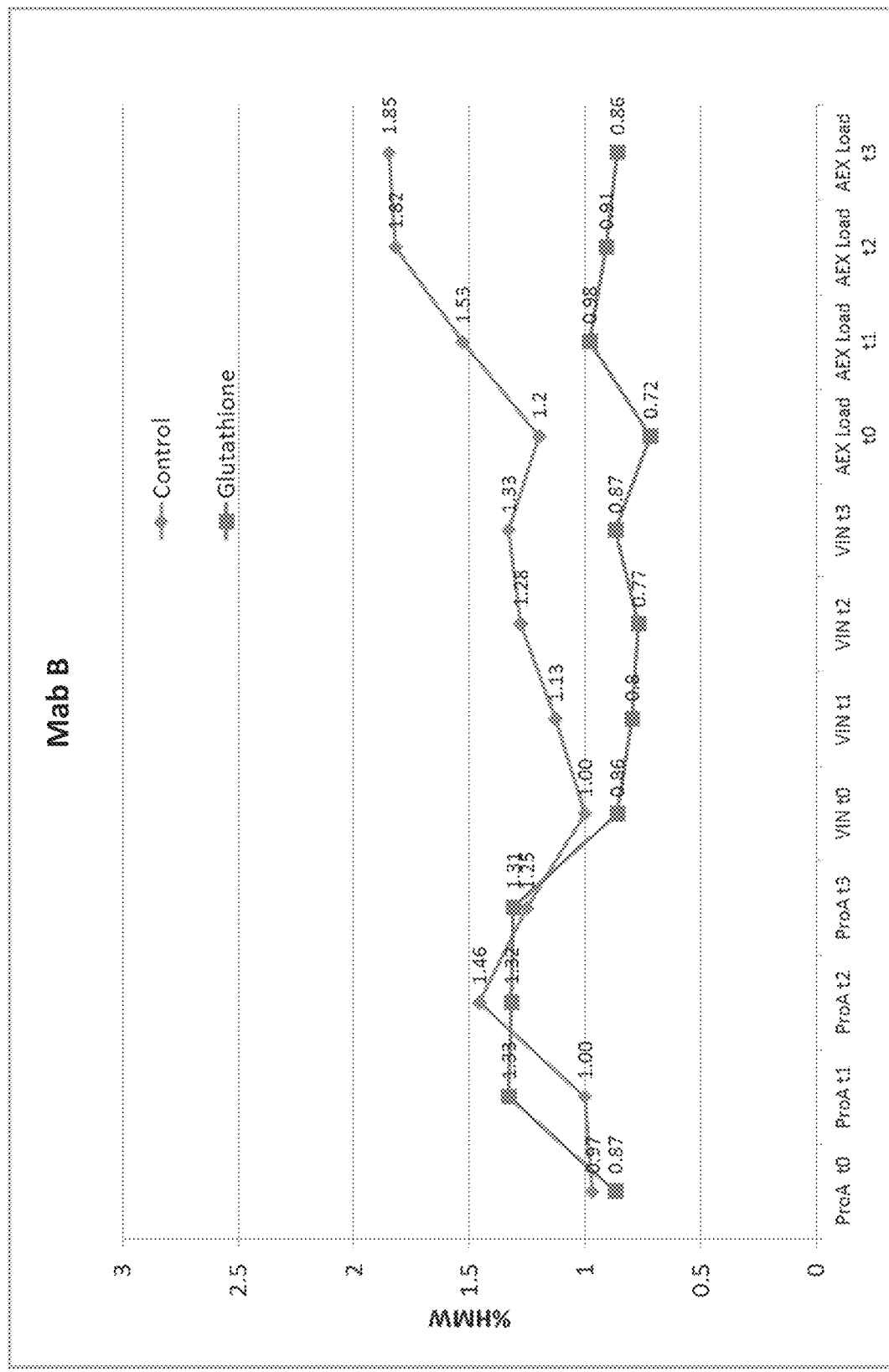
FIG. 6 is a graph showing the percentage of high molecular weight (MHW) aggregates detected in a solution comprising Mab B during an exemplary purification as shown in FIG. 2.
Figure 7:
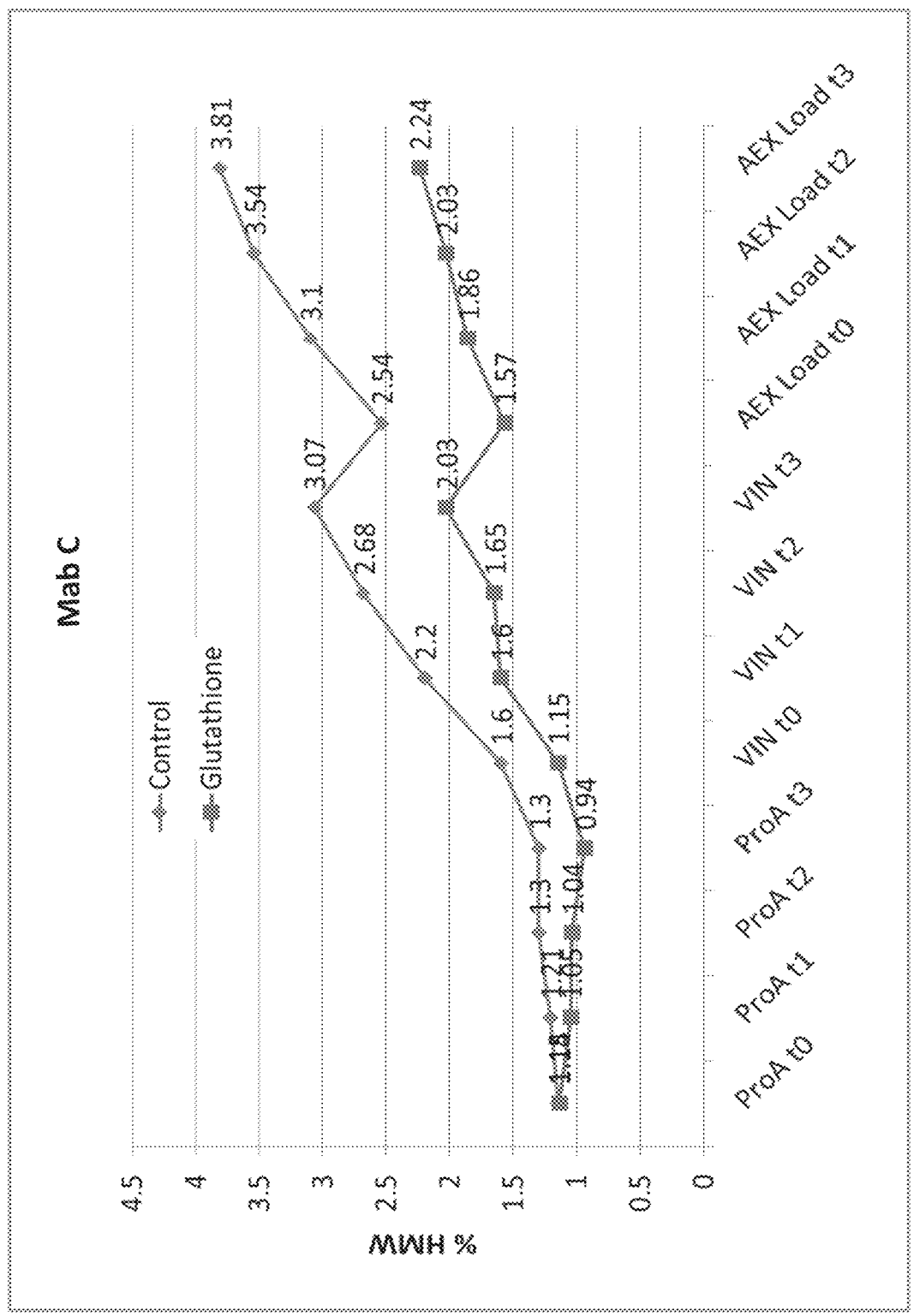
FIG. 7 is a graph showing the percentage of high molecular weight (MHW) aggregates detected in a solution comprising Mab C during an exemplary purification as shown in FIG. 2.

Spiking glutathione at the VIN pH 5.7 purification step for Mab A decreased the formation of % HMW aggregates (FIG. 5). Decreased % HMW aggregate formation was also detected during Mab B purification (FIG. 6) and Mab C purification (FIG. 7) when glutathione was spiked at the Mab Eluate step. Table 2 provides a summary of the effects of glutathione added at different purification steps on the % HMW aggregate formation for Mab A, Mab B, and Mab C.

Thus, the addition of glutathione at the Mab Eluate and VIN steps provides reduced rates of % HMW aggregate formation during antibody purification.

TABLE 2

Summary of purification conditions and aggregation results.

| Mab | IgG | pH Process step | Hold time (days) | Protein Concentration (mg/mL) | Δ % HMW NO GSH | Δ % HMW GSH | Slope NO GSH | Slope GSH |
|---|---|---|---|---|---|---|---|---|
| B | IgG1 | 3.5 Mab Eluate | 3 | 13.2 | 0.28 | 0.44 | 0.22 | 0.27 |
|   |      | 5.7 VIN pH 5.7 | 3 | 12.35 | 0.33 | 0.01 | 0.19 | −0.01 |
|   |      | 7.1 AEX Load | 3 | 11.7 | 0.65 | 0.14 | 0.40 | 0.09 |
| C | IgG1 | 3.5 Mab Eluate | 3 | 15.8 | 0.15 | −0.20 | 0.09 | −0.10 |
|   |      | 5.7 VIN pH 5.7 | 3 | 14.5 | 1.47 | 0.88 | 0.83 | 0.46 |
|   |      | 7.1 AEX Load | 3 | 13.8 | 1.27 | 0.67 | 0.73 | 0.37 |
| A | IgG1 | 3.5 Mab Eluate | 3 | 15.1 | −0.2 | 12.12 | −0.13 | 6.82 |
|   |      | 5.7 VIN pH 5.7 | 3 | 13.9 | 0.98 | −5.12 | 0.59 | −3.13 |
|   |      | 7.1 AEX Load | 3 | 13.6 | 0.45 | 0.14 | 0.24 | 0.06 |

TABLE 2-continued

Summary of purification conditions and aggregation results.

| Mab | IgG | pH | Process step | Hold time (days) | Protein Concentration (mg/mL) | Δ % HMW NO GSH | Δ % HMW GSH | Slope NO GSH | Slope GSH |
|---|---|---|---|---|---|---|---|---|---|
| C | IgG1 | 3.7 | Mab Eluate | 0 | 16.1 | NA | NA | NA | NA |
|   |   | 5.7 | VIN | 1 | 16.0 | 0.75 | 0.44 | NA | NA |
|   |   | 6.5 | AEX Load | 1 | 14.6 | 0.40 | 0.11 | NA | NA |
|   |   | 6.5 | AEX FT | 1 | 11.7 | 0.41 | 0.06 | NA | NA |
| C | IgG1 | 3.7 | Mab Eluate | 0 | 16.1 | NA | NA | NA | NA |
|   |   | 5.7 | VIN | 2 | 16.0 | 0.67 | 0.15 | 0.45 | 0.10 |
|   |   | 7.1 | AEX Load | 2 | 14.6 | 1.31 | 1.49 | 0.88 | 0.33 |

Example 3: Spiking Mab Eluates with Glutathione Reduced Percentages of High Molecular Weight (% HMW) Aggregate Formation Detected During the Purification Process To evaluate the effects of glutathione on high molecular weight (HMW) aggregate formation during multiple purification steps shown in FIG. 1, glutathione was spiked into the Mab B eluate and % HMW formation was monitored throughout the purification process. Un-spiked Mab B eluates were used as a control.

Figure 8:
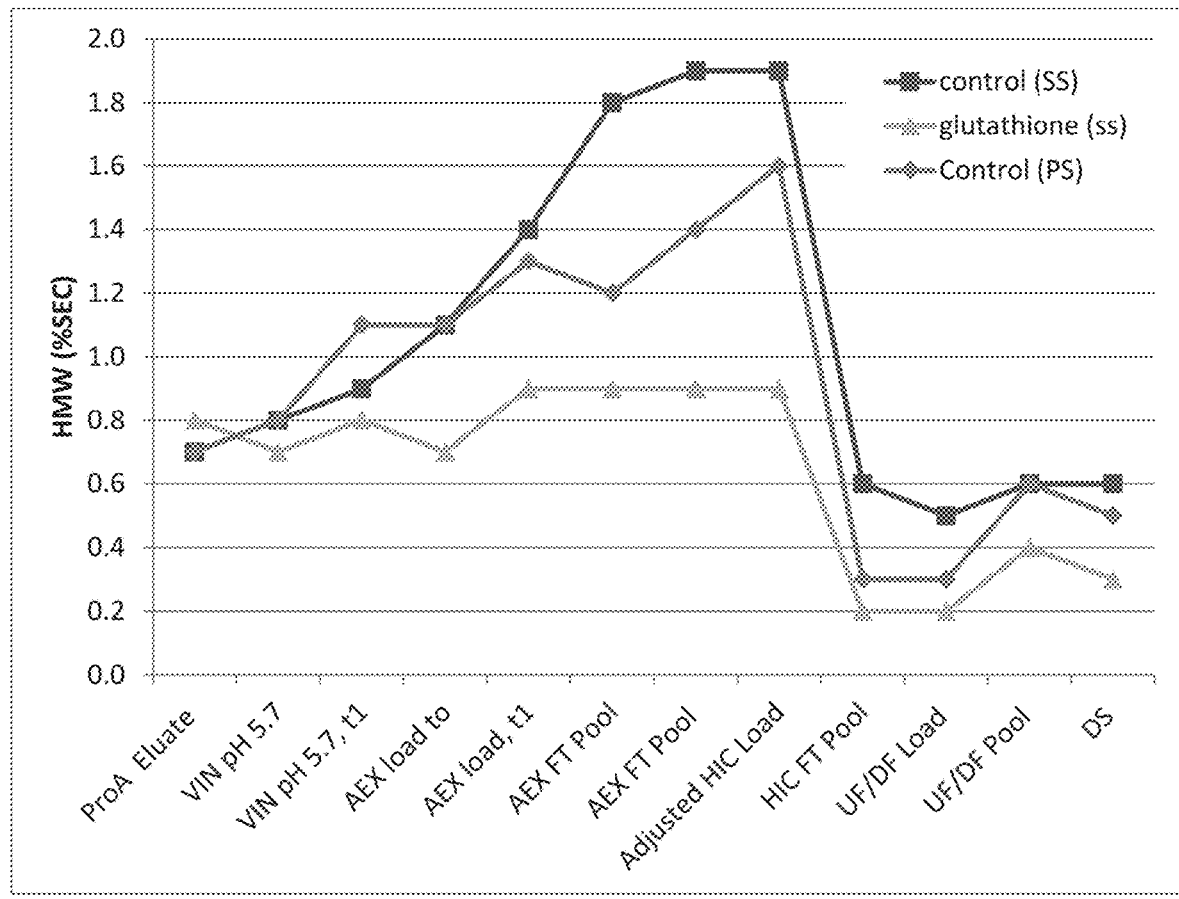
FIG. 8 is a graph showing the percentage of high molecular weight (MHW) aggregates detected during purification of Mab B in which the Mab eluate was spiked with glutathione (triangle). As a control, % HMW aggregates were detected in a purification of un-spiked Mab eluate (square).
Figure 9A:
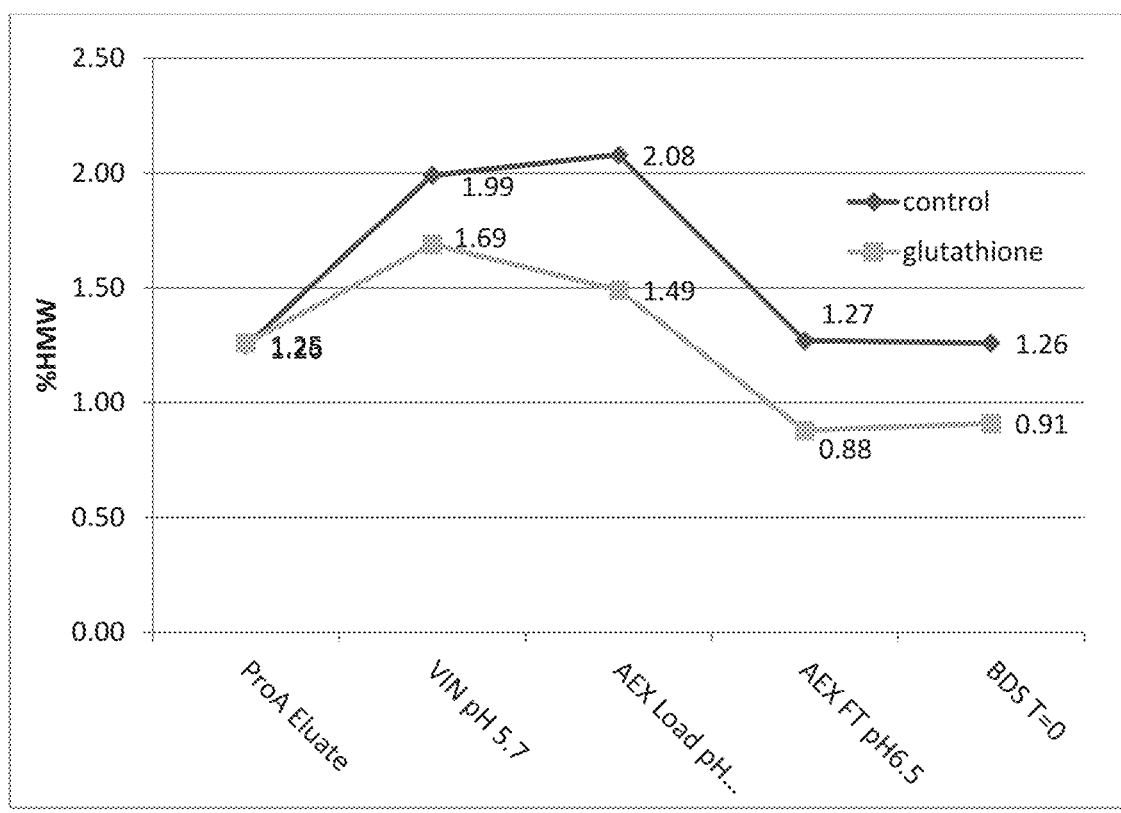
FIG. 9A is a graph showing the percentage of high molecular weight (MHW) aggregates detected during purification of Mab C in which the Mab eluate was spiked with glutathione (square). As a control, % HMW aggregates were detected in a purification of un-spiked Mab eluate (triangle). AEX load step was performed at pH 6.5.
Figure 9B:
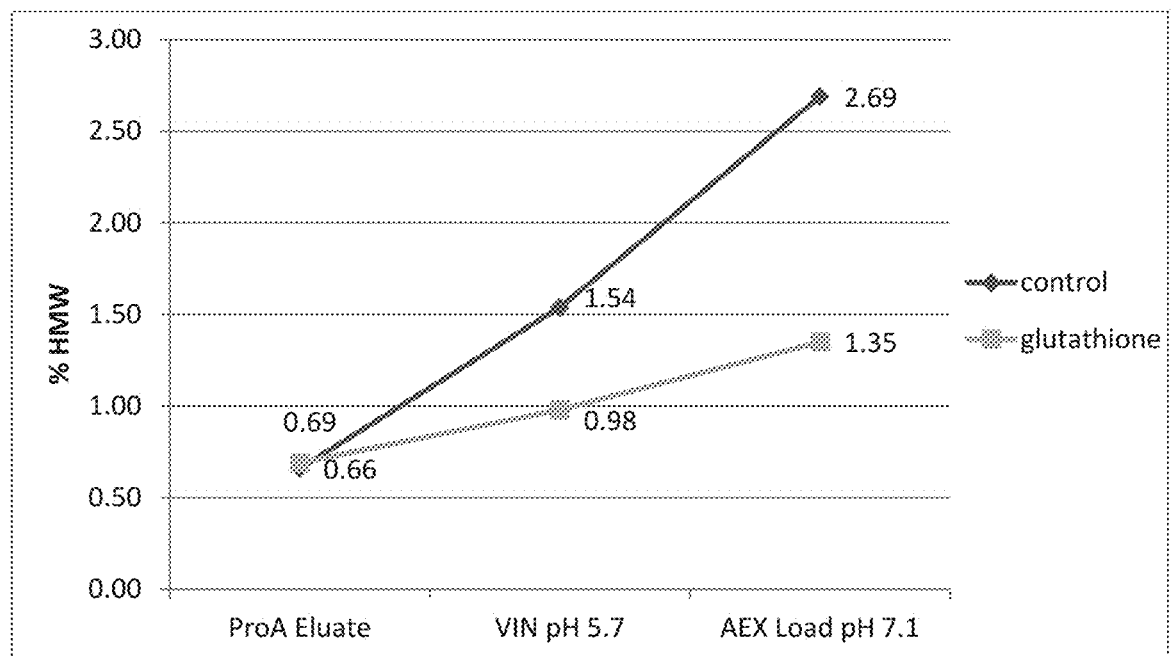
FIG. 9B is a graph showing the percentage of high molecular weight (MHW) aggregates detected during purification of Mab C in which the Mab eluate was spiked with glutathione (square). As a control, % HMW aggregates were detected in a purification of un-spiked Mab eluate (triangle). AEX load step was performed at pH 7.1.

For small scale purification of Mab B, the % HMW aggregates were reduced in the sample spiked with glutathione compared to a control, un-spiked, sample throughout the purification process (FIG. 8). Purification of Mab B eluates spiked with glutathione also showed reduced % HMW aggregate formation compared to a large scale pilot run without glutathione (FIG. 8). In another example, reduced % HMW aggregate formation was observed in Mab C eluates spiked with glutathione compared to control, un-spiked samples (FIGS. 9A-9B). Reduction in % HMW aggregates in the spiked Mab C samples were detected during ion exchange chromatography steps at both pH 6.5 (FIG. 9A) and pH 7.1 (FIG. 9B).

Thus, the addition of glutathione into the Mab eluate reduced the formation of % HMW aggregates during multiple steps of the purification process.

Example 4: Spiking Mab Eluates with Glutathione Allows Higher Column Loading and Yield To evaluate whether reduced % HMW aggregates in samples spiked with glutathione would allow higher loading of the antibody onto a chromatography column, Mab C was loaded onto the column at higher concentrations and the % HMW aggregate formation was monitored.

Figure 10:
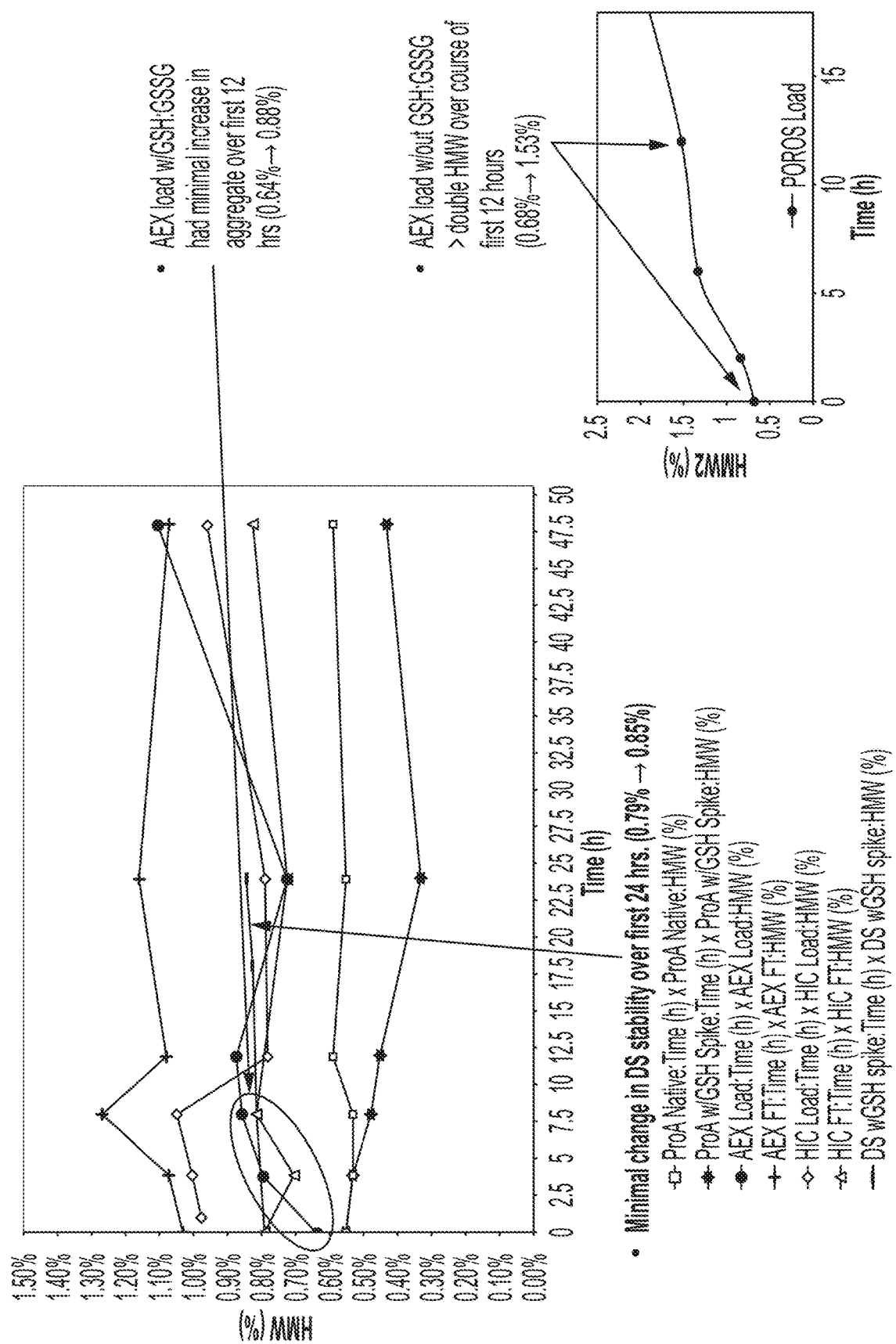
FIG. 10 is a graph showing the percentage of high molecular weight (MHW) aggregates detected in a solution comprising Mab C during the first 48 hours of the purification.

Reduced % HMW aggregate formation was detected over the initial 12 hours of Mab C purification using Mab C loads spiked with glutathione (FIG. 10). The % HMW aggregates doubled over the initial 12 hours of antibody purification for control, un-spiked Mab C loads (FIG. 10).

Mab C was loaded onto an affinity chromatography column (POROS) at 1300 g/L compared to typical loads of 500 g/L. Antibody yield was improved using higher column loads (Table 3). The yield from the column loaded at 1300 g/L was 94.5% compared to a 88% yield from a 500 g/L loaded column (6% difference in yield). Mab C was also loaded onto a hydrophobic interaction chromatography column (Capto Phenyl) at 500 g/L compared to typical loads of 200 g/L. The yield from the column loaded at 500 g/L was 93% compared to a 79% yield from a 200 g/L loaded column (13% difference in yield).

These results demonstrated that higher column loading and yield is possible for antibodies spiked with glutathione compared to control, un-spiked antibodies.

TABLE 3

Mab C process yield and performance.

| | Loading (g/L) | Mass Balance (%) | Yield (%) | Conc. (mg/ml) | Load HMW (%) | Pool HMW (%) | HCP (ppm) | DNA (ppb) | rPA (ppm) |
|---|---|---|---|---|---|---|---|---|---|
| native eluate | | | | 15.80 | | 0.55% | 1170.9 | 94.3 | 4.02 |
| AC Pool | 1406 | 99.47% | 94.50% | 13.48 | 0.64% | 1.03% | 67.2 | <LLOQ | 0.20 |
| HIC Pool | 500.3 | 100.33% | 93.00% | 11.60 | 0.98% | 0.79% | 6.4 | <LLOQ | 0.15 |
| DS (152 g/L) | | | | | | 0.79% | | | |

Figure 11:
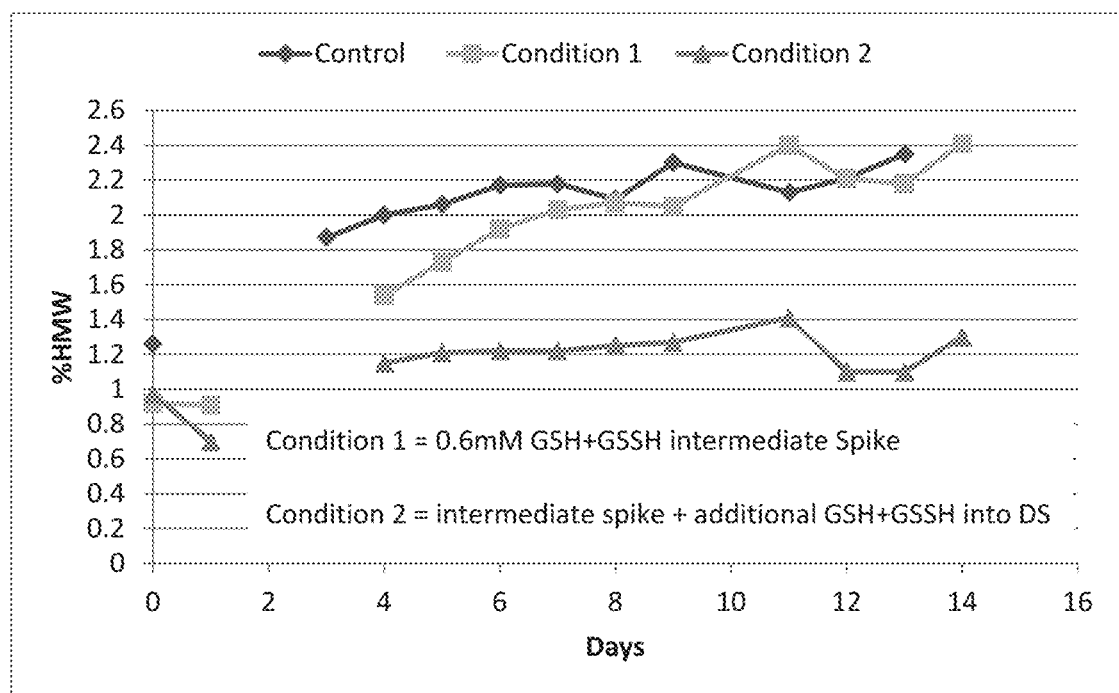
FIG. 11 is a graph showing the percentage of high molecular weight (MHW) aggregates detected in a sample comprising Mab C in which glutathione was added during purification (Condition 1) and in a sample comprising Mab C in which glutathione was added during at both the purification and drug substance (DS) steps (Condition 2).

Example 5: Additional Spike of Glutathione into the Bulk Drug Substance (BDS) from Spiked Intermediates has Less % HMW Formation During Stability Compared to Control and Spiked Intermediates without Additional Spike at BDS A process intermediate that was also spiked with glutathione was additionally spiked with glutathione at BDS (condition 2). This BDS was placed on stability at ambient for 14 days along with a control that had no glutathione spike in either the process intermediate or at BDS, and a sample that was spiked at the intermediate but had no additional spike at BDS (condition 1). The change in % HMW over 14 days was minimal for condition 2 compared to condition 1 and the control (FIG. 11).

These results demonstrated that additional spiked DS formulations have reduced % HMW aggregates compared to control, un-spiked DS formulations.

Example 6: High Molecular Weight Aggregate Formation at High Antibody Concentrations and During Stability The effects of glutathione on the percentage of high molecular weight (% HMW) aggregate formation during stability for various Mabs at high concentrations (e.g., greater than 150 mg/mL) was tested (Table 4). The effects of glutathione on the % HMW aggregate formation was also tested over pH 5-6 for several Mabs (Table 5).

TABLE 4

High molecular weight aggregate formation during stability.

| Mab | IgG | Protein Concentration (mg/mL) | pH | Storage Condition | Δ % HMW (No GSH) | Δ % HMW (GSH) | % decrease | Result |
|---|---|---|---|---|---|---|---|---|
| B | IgG1 | 165 | 5.5 | 2 m @ 25 deg | 2 | 0.48 | 76 | +++ |
| C | IgG1 | 150 | 5.5 | 2 m @ 25 deg | 1.32 | −0.33 | 125 | +++ |
| D | IgG1 | 150 | 5.5 | 2 m @ 25 deg | 2.69 | 2.27 | 16 | + |
| E | IgG4 | 150 | 5.7 | 2 m @ 25 deg | 1.88 | 0.95 | 49 | ++ |
| F | IgG1 | 150 | 6.5 | 2 m @ 25 deg | −0.2 | −0.88 |  | +++ |
| G | IgG1 | 150 | 5.5 | 2 m @ 25 deg | 0.82 | −0.25 | 130 | ++ |
| A | IgG1 | 150 | 6.5 | 2 m @ 25 deg | 1.06 | 0.6 | 43 | ++ |
| H | IgG1 | 150 | 6 | 2 m @ 25 deg | 0.22 | 0.07 | 68 | No change |
| I | IgG4 | 150 | 6 | 2 m @ 25 deg | 0.36 | 0.39 | −8 | No change |
| *J | IgG1 | 150 | 6.5 | 2 m @ 25 deg | 16.96 | 6.03 | − | --- |
| *K | fusion | 150 | 6.2 | 2 m @ 25 deg | 3.39 | 3.37 | 1 | No change |

*GSH:GSSG

TABLE 5

High molecular weight aggregate formation at various pH.

| Mab | IgG | pH | Formulation Result |
|---|---|---|---|
| B | IgG1 | 6.3 | No change |
| B | IgG1 | 5.5 | +++ |
| C | IgG1 | 5.5 | +++ |
| D | IgG1 | 5.5 | + |
| E | IgG4 | 5.7 | ++ |
| F | IgG1 | 6.5 | ++ |
| G | IgG1 | 5.5 | ++ |
| A | IgG1 | 6.5 | + |
| H | IgG1 | 6 | No change |
| I | IgG4 | 6 | No change |
| *J | IgG1 | 6.5 | -- |
| *K | fusion | 6.2 | No change |

*GSH:GSSG

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present disclosure, and without departing from the spirit and scope thereof, can make various changes and modifications of the present disclosure to adapt it to various usages and conditions. Thus, other embodiments are also within the claims.

EQUIVALENTS AND SCOPE

Those skilled in the art will recognize, or be able to ascertain using no more than routine experimentation, many equivalents to the specific embodiments of the present disclosure described herein. The scope of the present disclosure is not intended to be limited to the above description, but rather is as set forth in the appended claims.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. All references, patents and patent applications disclosed herein are incorporated by reference with respect to the subject matter for which each is cited, which in some cases may encompass the entirety of the document. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

The invention claimed is:

1. A method of reducing formation of high molecular weight antibody aggregates in an antibody sample, the method comprising:
   subjecting an antibody sample to viral inactivation at a pH of less than 5.0;
   neutralizing the antibody sample to produce a neutralized antibody sample having a pH of greater than 5.0; and
   introducing an additive into the neutralized antibody sample, wherein the additive is selected from the group consisting of cysteine, L-cysteine, sulfur dioxide, hydrogen sulfide, bisulfite, and glutathione.

2. The method of claim 1, wherein the neutralized antibody sample has a pH of 5.7.

3. The method of claim 1, wherein the additive comprises oxidized and reduced forms of the additive.

4. The method of claim 3, wherein the ratio of oxidized to reduced forms of the additive is between about 1:1 and about 1:10.

5. The method of claim 1, wherein the additive comprises oxidized and reduced forms of glutathione.

6. The method of claim 5, wherein the ratio of oxidized to reduced forms of glutathione is about 1:1, about 1:2, about 1:3, about 1:4, about 1:5, about 1:6, about 1:7, about 1:8, about 1:9, or about 1:10.

7. The method of claim 1, wherein the additive is added to the neutralized antibody sample at a final concentration of between about 0.01 mM and about 1 mM.

8. The method of claim 1, further comprising determining a level of high molecular weight aggregates in the antibody sample.

9. The method of claim 1, further comprising, after introducing the additive into the neutralized antibody sample:
   providing a solution comprising an antibody of the neutralized antibody sample; and
   subjecting the solution to one or more chromatographic separations.

10. The method of claim 9, wherein the one or more chromatographic separations are selected from affinity chromatography, ion exchange chromatography, and hydrophobic interaction chromatography.

11. The method of claim 1, wherein the antibody sample comprises a monoclonal antibody, a chimeric antibody, a human antibody, or a humanized antibody.

12. The method of claim 1, wherein the antibody sample comprises an antibody selected from the group consisting of anti-α-synuclein, anti-BDCA2, anti-LINGO, anti-LINGO-1, abciximab, adalimumab, aducanumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, omalizumab, palivizumab, panitumumab, ranibizumab, rituximab, tositumomab, and trastuzumab.

13. A method of reducing formation of high molecular weight antibody aggregates in an antibody sample, the method comprising:
   subjecting an antibody sample to viral inactivation at a pH of less than 5.0, wherein the antibody sample comprises a non-human antibody;
   neutralizing the antibody sample to produce a neutralized antibody sample having a pH of greater than 5.0; and
   introducing an additive into the neutralized antibody sample, wherein the additive is selected from the group consisting of cysteine, L-cysteine, sulfur dioxide, hydrogen sulfide, bisulfite, and glutathione.

* * * * *